(12) United States Patent
Hennessey et al.

(10) Patent No.: US 8,721,794 B2
(45) Date of Patent: May 13, 2014

(54) PRODUCTION OF HIGH SOLIDS SYRUP FROM LIGNOCELLULOSIC BIOMASS HYDROLYSATE FERMENTATION BROTH

(75) Inventors: Susan Marie Hennessey, Avondale, PA (US); Rahul B. Kasat, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 271 days.

(21) Appl. No.: 13/093,118

(22) Filed: Apr. 25, 2011

(65) Prior Publication Data

US 2012/0102823 A1 May 3, 2012

Related U.S. Application Data

(60) Provisional application No. 61/328,799, filed on Apr. 28, 2010.

(51) Int. Cl.
*B01D 1/00* (2006.01)
*B01D 3/00* (2006.01)
*C10L 1/00* (2006.01)
*C12P 19/00* (2006.01)

(52) U.S. Cl.
USPC ............ 127/29; 127/30; 127/32; 127/33; 127/36; 127/46.1; 210/770; 210/774; 210/805; 210/806; 203/39; 203/43; 424/725; 426/61; 426/429; 426/489; 426/658; 44/307; 44/605; 435/136; 435/161; 435/165

(58) Field of Classification Search
USPC .......... 210/632, 634, 770, 774, 805, 806; 159/47.1; 203/39, 43, 47, 98; 127/30, 127/46.1, 53, 55, 57, 29, 32, 33, 36, 37; 426/61, 429, 489, 658; 435/61, 136, 435/159–165; 568/913, 916; 44/307, 605, 44/606; 424/130.1, 725, 769, 780
See application file for complete search history.

(56) References Cited

U.S. PATENT DOCUMENTS

| 2,658,840 | A | * | 11/1953 | Perry | 427/207.1 |
|---|---|---|---|---|---|
| 2,846,409 | A | * | 8/1958 | Herschler et al. | 525/54.1 |
| 3,025,250 | A | * | 3/1962 | Herrick et al. | 524/16 |
| 3,152,150 | A | | 10/1964 | Wilson et al. | |
| 3,682,856 | A | * | 8/1972 | Adams et al. | 524/702 |
| 3,838,077 | A | * | 9/1974 | Hofteizer et al. | 525/54.3 |
| 4,374,981 | A | | 2/1983 | Tsuda et al. | |
| 5,662,810 | A | | 9/1997 | Willgohs | |
| 5,770,010 | A | * | 6/1998 | Jelks | 162/6 |
| 7,497,955 | B2 | | 3/2009 | Scheimann et al. | |
| 7,807,735 | B2 | * | 10/2010 | Wantling | 524/45 |
| 8,236,977 | B2 | * | 8/2012 | Woods et al. | 554/8 |
| 2003/0059512 | A1 | | 3/2003 | Kopf et al. | |
| 2003/0162271 | A1 | | 8/2003 | Zhang et al. | |
| 2006/0057251 | A1 | | 3/2006 | Dawley et al. | |
| 2007/0000769 | A1 | | 1/2007 | Brown | |
| 2007/0031918 | A1 | | 2/2007 | Dunson, Jr. et al. | |
| 2007/0175825 | A1 | | 8/2007 | Denney | |
| 2007/0254089 | A1 | | 11/2007 | Hickey et al. | |
| 2008/0153149 | A1 | | 6/2008 | Van Leeuwen et al. | |
| 2009/0008235 | A1 | | 1/2009 | Goel et al. | |
| 2009/0017164 | A1 | | 1/2009 | Schisler et al. | |
| 2009/0155428 | A1 | * | 6/2009 | Mitchell et al. | 426/103 |
| 2009/0246846 | A1 | | 10/2009 | Viitanen et al. | |
| 2009/0305370 | A1 | | 12/2009 | Grady et al. | |

FOREIGN PATENT DOCUMENTS

| CN | 101348429 A | 1/2009 |
|---|---|---|
| GB | 982712 | 8/1962 |
| GB | 1413236 | 11/1975 |
| WO | 2004039959 A2 | 5/2004 |
| WO | 2004088230 A2 | 10/2004 |
| WO | 2008076716 A1 | 6/2008 |
| WO | 2008100837 A2 | 8/2008 |
| WO | 2009108748 A2 | 9/2009 |
| WO | 2009149270 A2 | 12/2009 |

OTHER PUBLICATIONS

U.S. Appl. No. 61/328,804, filed Apr. 28, 2010.
PCT International Search Report dated Aug. 2, 2011, PCT International Application No. PCT/US2011/034056.
PCT International Search Report dated Aug. 9, 2011, PCT International Application No. PCT/US2011/034061.

* cited by examiner

*Primary Examiner* — Joseph Drodge

(57) ABSTRACT

Lignocellulosic biomass hydrolysate fermentation broth may be processed to produce a high solids syrup having relatively low viscosity that has a high energy content and may be burned in a fermentation production process. The high solids syrup was achieved through liquid/solid separation of broth or depleted broth producing a thin stillage with low suspended solids allowing evaporation to high solids while maintaining low viscosity.

15 Claims, No Drawings

SEQUENCE LISTING

<160> NUMBER OF SEQ ID NOS: 8

<210> SEQ ID NO 1
<211> LENGTH: 347
<212> TYPE: PRT
<213> ORGANISM: Trichoderma reesei

<400> SEQUENCE: 1

Met Lys Ala Asn Val Ile Leu Cys Leu Leu Ala Pro Leu Val Ala Ala
1               5                   10                  15

Leu Pro Thr Glu Thr Ile His Leu Asp Pro Glu Leu Ala Ala Leu Arg
            20                  25                  30

Ala Asn Leu Thr Glu Arg Thr Ala Asp Leu Trp Asp Arg Gln Ala Ser
        35                  40                  45

Gln Ser Ile Asp Gln Leu Ile Lys Arg Lys Gly Lys Leu Tyr Phe Gly
    50                  55                  60

Thr Ala Thr Asp Arg Gly Leu Leu Gln Arg Glu Lys Asn Ala Ala Ile
65                  70                  75                  80

Ile Gln Ala Asp Leu Gly Gln Val Thr Pro Glu Asn Ser Met Lys Trp
                85                  90                  95

Gln Ser Leu Glu Asn Asn Gln Gly Gln Leu Asn Trp Gly Asp Ala Asp
            100                 105                 110

Tyr Leu Val Asn Phe Ala Gln Asn Gly Lys Ser Ile Arg Gly His
        115                 120                 125

Thr Leu Ile Trp His Ser Gln Leu Pro Ala Trp Val Asn Asn Ile Asn
    130                 135                 140

Asn Ala Asp Thr Leu Arg Gln Val Ile Arg Thr His Val Ser Thr Val
145                 150                 155                 160

Val Gly Arg Tyr Lys Gly Lys Ile Arg Ala Trp Asp Val Val Asn Glu
                165                 170                 175

Ile Phe Asn Glu Asp Gly Thr Leu Arg Ser Ser Val Phe Ser Arg Leu
            180                 185                 190

Leu Gly Glu Glu Phe Val Ser Ile Ala Phe Arg Ala Ala Arg Asp Ala
        195                 200                 205

Asp Pro Ser Ala Arg Leu Tyr Ile Asn Asp Tyr Asn Leu Asp Arg Ala
    210                 215                 220

Asn Tyr Gly Lys Val Asn Gly Leu Lys Thr Tyr Val Ser Lys Trp Ile
225                 230                 235                 240

Ser Gln Gly Val Pro Ile Asp Gly Ile Gly Ser Gln Ser His Leu Ser
                245                 250                 255

Gly Gly Gly Gly Ser Gly Thr Leu Gly Ala Leu Gln Gln Leu Ala Thr
            260                 265                 270

Val Pro Val Thr Glu Leu Ala Ile Thr Glu Leu Asp Ile Gln Gly Ala
        275                 280                 285

Pro Thr Thr Asp Tyr Thr Gln Val Gln Ala Cys Leu Ser Val Ser
    290                 295                 300

Lys Cys Val Gly Ile Thr Val Trp Gly Ile Ser Asp Lys Asp Ser Trp
305                 310                 315                 320

Arg Ala Ser Thr Asn Pro Leu Leu Phe Asp Ala Asn Phe Asn Pro Lys
                325                 330                 335

Pro Ala Tyr Asn Ser Ile Val Gly Ile Leu Gln
            340                 345

<210> SEQ ID NO 2

-continued

<211> LENGTH: 766
<212> TYPE: PRT
<213> ORGANISM: Fusarium verticilloides

<400> SEQUENCE: 2

```
Met Leu Leu Asn Leu Gln Val Ala Ala Ser Ala Leu Ser Leu Ser Leu
1               5                   10                  15

Leu Gly Gly Leu Ala Glu Ala Ala Thr Pro Tyr Thr Leu Pro Asp Cys
            20                  25                  30

Thr Lys Gly Pro Leu Ser Lys Asn Gly Ile Cys Asp Thr Ser Leu Ser
        35                  40                  45

Pro Ala Lys Arg Ala Ala Ala Leu Val Ala Ala Leu Thr Pro Glu Glu
    50                  55                  60

Lys Val Gly Asn Leu Val Ser Asn Ala Thr Gly Ala Pro Arg Ile Gly
65                  70                  75                  80

Leu Pro Arg Tyr Asn Trp Trp Asn Glu Ala Leu His Gly Leu Ala Gly
                85                  90                  95

Ser Pro Gly Gly Arg Phe Ala Asp Thr Pro Pro Tyr Asp Ala Ala Thr
            100                 105                 110

Ser Phe Pro Met Pro Leu Leu Met Ala Ala Ala Phe Asp Asp Asp Leu
        115                 120                 125

Ile His Asp Ile Gly Asn Val Val Gly Thr Glu Ala Arg Ala Phe Thr
    130                 135                 140

Asn Gly Gly Trp Arg Gly Val Asp Phe Trp Thr Pro Asn Val Asn Pro
145                 150                 155                 160

Phe Lys Asp Pro Arg Trp Gly Arg Gly Ser Glu Thr Pro Gly Glu Asp
                165                 170                 175

Ala Leu His Val Ser Arg Tyr Ala Arg Tyr Ile Val Arg Gly Leu Glu
            180                 185                 190

Gly Asp Lys Glu Gln Arg Arg Ile Val Ala Thr Cys Lys His Tyr Ala
        195                 200                 205

Gly Asn Asp Phe Glu Asp Trp Gly Gly Phe Thr Arg His Asp Phe Asp
    210                 215                 220

Ala Lys Ile Thr Pro Gln Asp Leu Ala Glu Tyr Tyr Val Arg Pro Phe
225                 230                 235                 240

Gln Glu Cys Thr Arg Asp Ala Lys Val Gly Ser Ile Met Cys Ala Tyr
                245                 250                 255

Asn Ala Val Asn Gly Ile Pro Ala Cys Ala Asn Ser Tyr Leu Gln Glu
            260                 265                 270

Thr Ile Leu Arg Gly His Trp Asn Trp Thr Arg Asp Asn Asn Trp Ile
        275                 280                 285

Thr Ser Asp Cys Gly Ala Met Gln Asp Ile Trp Gln Asn His Lys Tyr
    290                 295                 300

Val Lys Thr Asn Ala Glu Gly Ala Gln Val Ala Phe Glu Asn Gly Met
305                 310                 315                 320

Asp Ser Ser Cys Glu Tyr Thr Thr Thr Ser Asp Val Ser Asp Ser Tyr
                325                 330                 335

Lys Gln Gly Leu Leu Thr Glu Lys Leu Met Asp Arg Ser Leu Lys Arg
            340                 345                 350

Leu Phe Glu Gly Leu Val His Thr Gly Phe Phe Asp Gly Ala Lys Ala
        355                 360                 365

Gln Trp Asn Ser Leu Ser Phe Ala Asp Val Asn Thr Lys Glu Ala Gln
    370                 375                 380

Asp Leu Ala Leu Arg Ser Ala Val Glu Gly Ala Val Leu Leu Lys Asn
385                 390                 395                 400
```

Asp Gly Thr Leu Pro Leu Lys Leu Lys Lys Asp Ser Val Ala Met
            405                 410                 415

Ile Gly Phe Trp Ala Asn Asp Thr Ser Lys Leu Gln Gly Gly Tyr Ser
                420                 425                 430

Gly Arg Ala Pro Phe Leu His Ser Pro Leu Tyr Ala Ala Glu Lys Leu
            435                 440                 445

Gly Leu Asp Thr Asn Val Ala Trp Gly Pro Thr Leu Gln Asn Ser Ser
450                 455                 460

Ser His Asp Asn Trp Thr Thr Asn Ala Val Ala Ala Lys Lys Ser
465                 470                 475                 480

Asp Tyr Ile Leu Tyr Phe Gly Gly Leu Asp Ala Ser Ala Ala Gly Glu
                485                 490                 495

Asp Arg Asp Arg Glu Asn Leu Asp Trp Pro Glu Ser Gln Leu Thr Leu
            500                 505                 510

Leu Gln Lys Leu Ser Ser Leu Gly Lys Pro Leu Val Val Ile Gln Leu
            515                 520                 525

Gly Asp Gln Val Asp Asp Thr Ala Leu Leu Lys Asn Lys Lys Ile Asn
            530                 535                 540

Ser Ile Leu Trp Val Asn Tyr Pro Gly Gln Asp Gly Gly Thr Ala Val
545                 550                 555                 560

Met Asp Leu Leu Thr Gly Arg Lys Ser Pro Ala Gly Arg Leu Pro Val
                565                 570                 575

Thr Gln Tyr Pro Ser Lys Tyr Thr Glu Gln Ile Gly Met Thr Asp Met
            580                 585                 590

Asp Leu Arg Pro Thr Lys Ser Leu Pro Gly Arg Thr Tyr Arg Trp Tyr
            595                 600                 605

Ser Thr Pro Val Leu Pro Tyr Gly Phe Gly Leu His Tyr Thr Lys Phe
            610                 615                 620

Gln Ala Lys Phe Lys Ser Asn Lys Leu Thr Phe Asp Ile Gln Lys Leu
625                 630                 635                 640

Leu Lys Gly Cys Ser Ala Gln Tyr Ser Asp Thr Cys Ala Leu Pro Pro
                645                 650                 655

Ile Gln Val Ser Val Lys Asn Thr Gly Arg Ile Thr Ser Asp Phe Val
            660                 665                 670

Ser Leu Val Phe Ile Lys Ser Glu Val Gly Pro Lys Pro Tyr Pro Leu
            675                 680                 685

Lys Thr Leu Ala Ala Tyr Gly Arg Leu His Asp Val Ala Pro Ser Ser
690                 695                 700

Thr Lys Asp Ile Ser Leu Glu Trp Thr Leu Asp Asn Ile Ala Arg Arg
705                 710                 715                 720

Gly Glu Asn Gly Asp Leu Val Val Tyr Pro Thr Tyr Thr Leu Leu
                725                 730                 735

Leu Asp Glu Pro Thr Gln Ala Lys Ile Gln Val Thr Leu Thr Gly Lys
            740                 745                 750

Lys Ala Ile Leu Asp Lys Trp Pro Gln Asp Pro Lys Ser Ala
755                 760                 765

<210> SEQ ID NO 3
<211> LENGTH: 350
<212> TYPE: PRT
<213> ORGANISM: Fusarium verticillioides

<400> SEQUENCE: 3

Met Gln Leu Lys Phe Leu Ser Ser Ala Leu Leu Leu Ser Leu Thr Gly
1               5                   10                  15

```
Asn Cys Ala Ala Gln Asp Thr Asn Asp Ile Pro Pro Leu Ile Thr Asp
                20                  25                  30

Leu Trp Ser Ala Asp Pro Ser Ala His Val Phe Glu Gly Lys Leu Trp
            35                  40                  45

Val Tyr Pro Ser His Asp Ile Glu Ala Asn Val Val Asn Gly Thr Gly
 50                  55                  60

Gly Ala Gln Tyr Ala Met Arg Asp Tyr His Thr Tyr Ser Met Lys Thr
 65                  70                  75                  80

Ile Tyr Gly Lys Asp Pro Val Ile Asp His Gly Val Ala Leu Ser Val
                85                  90                  95

Asp Asp Val Pro Trp Ala Lys Gln Gln Met Trp Ala Pro Asp Ala Ala
               100                 105                 110

Tyr Lys Asn Gly Lys Tyr Tyr Leu Tyr Phe Pro Ala Lys Asp Lys Asp
               115                 120                 125

Glu Ile Phe Arg Ile Gly Val Ala Val Ser Asn Lys Pro Ser Gly Pro
130                 135                 140

Phe Lys Ala Asp Lys Ser Trp Ile Pro Gly Thr Tyr Ser Ile Asp Pro
145                 150                 155                 160

Ala Ser Tyr Val Asp Thr Asn Gly Glu Ala Tyr Leu Ile Trp Gly Gly
                165                 170                 175

Ile Trp Gly Gly Gln Leu Gln Ala Trp Gln Asp His Lys Thr Phe Asn
               180                 185                 190

Glu Ser Trp Leu Gly Asp Lys Ala Ala Pro Asn Gly Thr Asn Ala Leu
               195                 200                 205

Ser Pro Gln Ile Ala Lys Leu Ser Lys Asp Met His Lys Ile Thr Glu
210                 215                 220

Thr Pro Arg Asp Leu Val Ile Leu Ala Pro Glu Thr Gly Lys Pro Leu
225                 230                 235                 240

Gln Ala Glu Asp Asn Lys Arg Arg Phe Phe Glu Gly Pro Trp Val His
                245                 250                 255

Lys Arg Gly Lys Leu Tyr Tyr Leu Met Tyr Ser Thr Gly Asp Thr His
               260                 265                 270

Phe Leu Val Tyr Ala Thr Ser Lys Asn Ile Tyr Gly Pro Tyr Thr Tyr
               275                 280                 285

Gln Gly Lys Ile Leu Asp Pro Val Asp Gly Trp Thr Thr His Gly Ser
290                 295                 300

Ile Val Glu Tyr Lys Gly Gln Trp Trp Leu Phe Phe Ala Asp Ala His
305                 310                 315                 320

Thr Ser Gly Lys Asp Tyr Leu Arg Gln Val Lys Ala Arg Lys Ile Trp
                325                 330                 335

Tyr Asp Lys Asp Gly Lys Ile Leu Leu Thr Arg Pro Lys Ile
                340                 345                 350

<210> SEQ ID NO 4
<211> LENGTH: 660
<212> TYPE: PRT
<213> ORGANISM: Fusarium verticillioides

<400> SEQUENCE: 4

Met Val Arg Phe Ser Ser Ile Leu Ala Ala Ala Cys Phe Val Ala
 1               5                  10                  15

Val Glu Ser Val Asn Ile Lys Val Asp Ser Lys Gly Gly Asn Ala Thr
                20                  25                  30

Ser Gly His Gln Tyr Gly Phe Leu His Glu Asp Ile Asn Asn Ser Gly
            35                  40                  45
```

-continued

```
Asp Gly Gly Ile Tyr Ala Glu Leu Ile Arg Asn Arg Ala Phe Gln Tyr
    50                  55                  60

Ser Lys Lys Tyr Pro Val Ser Leu Ser Gly Trp Arg Pro Ile Asn Asp
65                  70                  75                  80

Ala Lys Leu Ser Leu Asn Arg Leu Asp Thr Pro Leu Ser Asp Ala Leu
                85                  90                  95

Pro Val Ser Met Asn Val Lys Pro Gly Lys Gly Lys Ala Lys Glu Ile
                100                 105                 110

Gly Phe Leu Asn Glu Gly Tyr Trp Gly Met Asp Val Lys Lys Gln Lys
            115                 120                 125

Tyr Thr Gly Ser Phe Trp Val Lys Gly Ala Tyr Lys Gly His Phe Thr
    130                 135                 140

Ala Ser Leu Arg Ser Asn Leu Thr Asp Asp Val Phe Gly Ser Val Lys
145                 150                 155                 160

Val Lys Ser Lys Ala Asn Lys Lys Gln Trp Val Glu His Glu Phe Val
                165                 170                 175

Leu Thr Pro Asn Lys Asn Ala Pro Asn Ser Asn Asn Thr Phe Ala Ile
                180                 185                 190

Thr Tyr Asp Pro Lys Gly Ala Asp Gly Ala Leu Asp Phe Asn Leu Ile
            195                 200                 205

Ser Leu Phe Pro Pro Thr Tyr Lys Gly Arg Lys Asn Gly Leu Arg Val
    210                 215                 220

Asp Leu Ala Glu Ala Leu Glu Gly Leu His Pro Ser Leu Leu Arg Phe
225                 230                 235                 240

Pro Gly Gly Asn Met Leu Glu Gly Asn Thr Asn Lys Thr Trp Trp Asp
                245                 250                 255

Trp Lys Asp Thr Leu Gly Pro Leu Arg Asn Arg Pro Gly Phe Glu Gly
            260                 265                 270

Val Trp Asn Tyr Gln Gln Thr His Gly Leu Gly Ile Leu Glu Tyr Leu
    275                 280                 285

Gln Trp Ala Glu Asp Met Asn Leu Glu Ile Ile Val Gly Val Tyr Ala
    290                 295                 300

Gly Leu Ser Leu Asp Gly Ser Val Thr Pro Lys Asp Gln Leu Gln Pro
305                 310                 315                 320

Leu Ile Asp Asp Ala Leu Asp Glu Ile Glu Phe Ile Arg Gly Pro Val
                325                 330                 335

Thr Ser Lys Trp Gly Lys Lys Arg Ala Glu Leu Gly His Pro Lys Pro
            340                 345                 350

Phe Arg Leu Ser Tyr Val Glu Val Gly Asn Glu Asp Trp Leu Ala Gly
    355                 360                 365

Tyr Pro Thr Gly Trp Asn Ser Tyr Lys Glu Tyr Arg Phe Pro Met Phe
    370                 375                 380

Leu Glu Ala Ile Lys Lys Ala His Pro Asp Leu Thr Val Ile Ser Ser
385                 390                 395                 400

Gly Ala Ser Ile Asp Pro Val Gly Lys Lys Asp Ala Gly Phe Asp Ile
                405                 410                 415

Pro Ala Pro Gly Ile Gly Asp Tyr His Pro Tyr Arg Glu Pro Asp Val
                420                 425                 430

Leu Val Glu Glu Phe Asn Leu Phe Asp Asn Asn Lys Tyr Gly His Ile
            435                 440                 445

Ile Gly Glu Val Ala Ser Thr His Pro Asn Gly Gly Thr Gly Trp Ser
    450                 455                 460

Gly Asn Leu Met Pro Tyr Pro Trp Trp Ile Ser Gly Val Gly Glu Ala
```

```
                465                 470                 475                 480
Val Ala Leu Cys Gly Tyr Glu Arg Asn Ala Asp Arg Ile Pro Gly Thr
                    485                 490                 495

Phe Tyr Ala Pro Ile Leu Lys Asn Glu Asn Arg Trp Gln Trp Ala Ile
                500                 505                 510

Thr Met Ile Gln Phe Ala Ala Asp Ser Ala Met Thr Thr Arg Ser Thr
            515                 520                 525

Ser Trp Tyr Val Trp Ser Leu Phe Ala Gly His Pro Met Thr His Thr
        530                 535                 540

Leu Pro Thr Thr Ala Asp Phe Asp Pro Leu Tyr Tyr Val Ala Gly Lys
545                 550                 555                 560

Asn Glu Asp Lys Gly Thr Leu Ile Trp Lys Gly Ala Ala Tyr Asn Thr
                565                 570                 575

Thr Lys Gly Ala Asp Val Pro Val Ser Leu Ser Phe Lys Gly Val Lys
            580                 585                 590

Pro Gly Ala Gln Ala Glu Leu Thr Leu Leu Thr Asn Lys Glu Lys Asp
        595                 600                 605

Pro Phe Ala Phe Asn Asp Pro His Lys Gly Asn Asn Val Val Asp Thr
    610                 615                 620

Lys Lys Thr Val Leu Lys Ala Asp Gly Lys Gly Ala Phe Asn Phe Lys
625                 630                 635                 640

Leu Pro Asn Leu Ser Val Ala Val Leu Glu Thr Leu Lys Lys Gly Lys
                645                 650                 655

Pro Tyr Ser Ser
            660

<210> SEQ ID NO 5
<211> LENGTH: 1352
<212> TYPE: DNA
<213> ORGANISM: Trichoderma reesei

<400> SEQUENCE: 5
atgaaagcaa acgtcatctt gtgcctcctg gcccccctgg tcgccgctct ccccaccgaa      60
accatccacc tcgaccccga gctcgccgct ctccgcgcca acctcaccga gcgaacagcc     120
gacctctggg accgccaagc ctctcaaagc atcgaccagc tcatcaagag aaaaggcaag     180
ctctactttg gcaccgccac cgaccgcggc tcctccaac gggaaaagaa cgcggccatc      240
atccaggcag acctcggcca ggtgacgccg agaacagca tgaagtggca gtcgctcgag      300
aacaaccaag gccagctgaa ctggggagac gccgactatc tcgtcaactt gcccagcaa      360 aacggcaagt cgatacgcgg ccacactctg atctggcact cgcagctgcc tgcgtgggtg    420
aacaatatca caacgcgga tactctgcgg caagtcatcc gcacccatgt ctctactgtg     480
gttgggcggt acaagggcaa gattcgtgct tgggtgagtt ttgaacacca catgcccctt   540
ttcttagtcc gctcctcctc tcttggaac ttctcacagt tatagccgta taacattc      600 gacaggaaat ttaggatgac aactactgac tgacttgtgt gtgtgatggc gataggacgt   660
ggtcaatgaa atcttcaacg aggatggaac gctgcgctct tcagtctttt ccaggctcct   720
cggcgaggag tttgtctcga ttgccttccg tgctgctcga gatgctgacc cttctgcccg    780
tctttacatc aacgactaca atctcgaccg cgccaactat ggcaaggtca cgggttgaa     840 gacttacgtc tccaagtgga tctctcaagg agttcccatt gacggtattg gtgagccacg   900 accctaaat gtcccccatt agagtctctt tctagagcca aggcttgaag ccattcaggg    960
actgacacga gagccttctc tacaggaagc cagtcccatc tcagcggcgg cggaggctct 1020
```

-continued

```
ggtacgctgg gtgcgctcca gcagctggca acggtacccg tcaccgagct ggccattacc    1080
gagctggaca ttcaggggc accgacgacg gattacaccc aagttgttca agcatgcctg     1140
agcgtctcca agtgcgtcgg catcaccgtg tggggcatca gtgacaaggt aagttgcttc    1200
ccctgtctgt gcttatcaac tgtaagcagc aacaactgat gctgtctgtc tttacctagg    1260
actcgtggcg tgccagcacc aaccctcttc tgtttgacgc aaacttcaac cccaagccgg    1320
catataacag cattgttggc atcttacaat ag                                  1352
```

<210> SEQ ID NO 6
<211> LENGTH: 2358
<212> TYPE: DNA
<213> ORGANISM: Fusarium verticillioides

<400> SEQUENCE: 6

```
atgctgctca atcttcaggt cgctgccagc gctttgtcgc tttctctttt aggtggattg      60
gctgaggctg ctacgccata tacccttccg gactgtacca aaggacccttt gagcaagaat     120 ggaatctgcg atacttcgtt atctccagct aaaagagcgg ctgctctagt tgctgctctg    180
acgcccgaag agaaggtggg caatctggtc aggtaaaaata taccccccc cataatcact    240 attcggagat tggagctgac ttaacgcagc aatgcaactg gtgcaccaag aatcggactt    300
ccaaggtaca actggtggaa cgaagccctt catggcctcg ctggatctcc aggtggtcgc    360
tttgccgaca ctcctcccta cgacgcggcc acatcatttc ccatgcctct tctcatggcc    420
gctgctttcg acgatgatct gatccacgat atcggcaacg tcgtcggcac cgaagcgcgt    480
gcgttcacta acggcggttg gcgcggagtc gacttctgga cacccaacgt caacccttt     540 aaagatcctc gctggggtcg tggctccgaa actccaggtg aagatgccct tcatgtcagc    600
cggtatgctc gctatatcgt caggggtctc gaaggcgata aggagcaacg acgtattgtt    660
gctacctgca agcactatgc tggaaacgac tttgaggact ggggaggctt cacgcgtcac    720
gactttgatg ccaagattac tcctcaggac ttggctgagt actacgtcag gcctttccag    780
gagtgcaccc gtgatgcaaa ggttggttcc atcatgtgcg cctacaatgc cgtgaacggc    840
attcccgcat gcgcaaactc gtatctgcag gagacgatcc tcagagggca ctggaactgg    900
acgcgcgata caactggat cactagtgat tgtggcgcca tgcaggatat ctggcagaat    960
cacaagtatg tcaagaccaa cgctgaaggt gcccaggtag cttttgagaa cggcatggat    1020
tctagctgcg agtatactac taccagcgat gtctccgatt cgtacaagca aggcctcttg    1080
actgagaagc tcatggatcg ttcgttgaag cgccttttcg aagggcttgt tcatactggt    1140
ttctttgacg gtgccaaagc gcaatggaac tcgctcagtt ttgcggatgt caacaccaag    1200
gaagctcagg atcttgcact cagatctgct gtggaggtg ctgttcttct taagaatgac    1260
ggcactttgc ctctgaagct caagaagaag gatagtgttg caatgatcgg attctgggcc    1320
aacgatactt ccaagctgca gggtggttac agtggacgtg ctccgttcct ccacagcccg    1380
ctttatgcag ctgagaagct tggtcttgac accaacgtgg cttggggtcc gacactgcag    1440
aacagctcat ctcatgataa ctggaccacc aatgctgttg ctgcggcgaa gaagtctgat    1500
tacattctct actttggtgg tcttgacgcc tctgctgctg gcgaggacag agatcgtgag    1560
aaccttgact ggcctgagag ccagctgacc cttcttcaga agctctctag tctcggcaag    1620
ccactggttg ttatccagct tggtgatcaa gtcgatgaca ccgctcttt gaagaacaag    1680 aagattaaca gtattctttg ggtcaattac cctggtcagg atggcggcac tgcagtcatg    1740
gacctgctca ctggacgaaa gagtcctgct ggccgactac ccgtcacgca atatcccagt    1800
```

-continued

```
aaatacactg agcagattgg catgactgac atggacctca gacctaccaa gtcgttgcca   1860
gggagaactt atcgctggta ctcaactcca gttcttccct acggctttgg cctccactac   1920
accaagttcc aagccaagtt caagtccaac aagttgacgt ttgacatcca gaagcttctc   1980
aagggctgca gtgctcaata ctccgatact tgcgcgctgc cccccatcca agttagtgtc   2040
aagaacaccg gccgcattac ctccgacttt gtctctctgg tctttatcaa gagtgaagtt   2100
ggacctaagc cttaccctct caagaccctt gcggcttatg gtcgcttgca tgatgtcgcg   2160
ccttcatcga cgaaggatat ctcactggag tggacgttgg ataacattgc gcgacgggga   2220
gagaatggtg atttggttgt ttatcctggg acttacactc tgttgctgga tgagcctacg   2280
caagccaaga tccaggttac gctgactgga aagaaggcta ttttggataa gtggcctcaa   2340
gaccccaagt ctgcgtaa                                                 2358
```

```
<210> SEQ ID NO 7
<211> LENGTH: 1053
<212> TYPE: DNA
<213> ORGANISM: Fusarium verticillioides

<400> SEQUENCE: 7
atgcagctca agtttctgtc ttcagcattg ttgctgtctt tgaccggcaa ttgcgctgcg     60
caagacacta atgatatccc tcctctgatc accgacctct ggtctgcgga tccctcggct    120
catgttttcg agggcaaact ctgggtttac ccatctcacg acatcgaagc caatgtcgtc    180
aacggcaccg gaggcgctca gtacgccatg agagattatc acacctattc catgaagacc    240
atctatggaa aagatcccgt tatcgaccat ggcgtcgctc tgtcagtcga tgatgtccca    300
tgggccaagc agcaaatgtg ggctcctgac gcagcttaca agaacggcaa atattatctc    360
tacttccccg ccaaggataa agatgagatc ttcagaattg gagttgctgt ctccaacaag    420
cccagcggtc ctttcaaggc cgacaagagc tggatccccg gtacttacag tatcgatcct    480
gctagctatg tcgacactaa tggcgaggca tacctcatct ggggcggtat ctggggcggc    540
cagcttcagg cctggcagga tcacaagacc tttaatgagt cgtggctcgg cgacaaagct    600
gctcccaacg gcaccaacgc cctatctcct cagatcgcca agctaagcaa ggacatgcac    660
aagatcaccg agacaccccg cgatctcgtc atcctggccc ccgagacagg caagcccctt    720
caagcagagg acaataagcg acgatttttc gaggggccct gggttcacaa gcgcggcaag    780
ctgtactacc tcatgtactc taccggcgac acgcacttcc tcgtctacgc gacttccaag    840
aacatctacg gtccttatac ctatcagggc aagattctcg accctgttga tgggtggact    900
acgcatggaa gtattgttga gtacaaggga cagtggtggt tgttctttgc ggatgcgcat    960
acttctggaa aggattatct gagacaggtt aaggcgagga agatctggta tgacaaggat   1020
ggcaagattt tgcttactcg tcctaagatt tag                                1053
```

```
<210> SEQ ID NO 8
<211> LENGTH: 2186
<212> TYPE: DNA
<213> ORGANISM: Fusarium verticillioides

<400> SEQUENCE: 8
atggttcgct tcagttcaat cctagcggct gcggcttgct tcgtggctgt tgagtcagtc     60
aacatcaagg tcgacagcaa gggcggaaac gctactagcg gtcaccaata tggcttcctt    120
cacgaggttg gtattgacac accactggcg atgattggga tgctaacttg gagctaggat    180
atcaacaatt ccggtgatgg tggcatctac gctgagctca tccgcaatcg tgctttccag    240
```

```
tacagcaaga aatacccgt ttctctatct ggctggagac ccatcaacga tgctaagctc    300
tccctcaacc gtctcgacac tcctctctcc gacgctctcc ccgtttccat gaacgtgaag    360
cctggaaagg gcaaggccaa ggagattggt ttcctcaacg agggttactg gggaatggat    420
gtcaagaagc aaaagtacac tggctctttc tgggttaagg gcgcttacaa gggccacttt    480
acagcttctt tgcgatctaa ccttaccgac gatgtctttg gcagcgtcaa ggtcaagtcc    540
aaggccaaca agaagcagtg ggttgagcat gagtttgtgc ttactcctaa caagaatgcc    600
cctaacagca caacacttt tgctatcacc tacgatccca aggtgagtaa caatcaaaac    660
tgggacgtga tgtatactga caatttgtag ggcgctgatg gagctcttga cttcaacctc    720
attagcttgt tccctcccac ctacaagggc cgcaagaacg gtcttcgagt tgatcttgcc    780
gaggctctcg aaggtctcca ccccgtaagg tttaccgtct cacgtgtatc gtgaacagtc    840
gctgacttgt agaaaagagc ctgctgcgct tccccggtgg taacatgctc gagggcaaca    900
ccaacaagac ctggtgggac tggaaggata ccctcggacc tctccgcaac cgtcctggtt    960
tcgagggtgt ctggaactac cagcagaccc atggtcttgg aatcttggag tacctccagt   1020
gggctgagga catgaaccttt gaaatcagta ggttctataa aattcagtga cggttatgtg   1080
catgctaaca gatttcagtt gtcggtgtct acgctggcct ctccctcgac ggctccgtca   1140
cccccaagga ccaactccag cccctcatcg acgacgcgct cgacgagatc gaattcatcc   1200
gaggtcccgt cacttcaaag tggggaaaga gcgcgctga gctcggccac cccaagcctt    1260
tcagactctc ctacgttgaa gtcggaaacg aggactggct cgctggttat cccactggct   1320
ggaactctta caaggagtac cgcttcccca tgttcctcga ggctatcaag aaagctcacc   1380
ccgatctcac cgtcatctcc tctggtgctt ctattgaccc cgttggtaag aaggatgctg   1440
gtttcgatat tcctgctcct ggaatcggtg actaccaccc ttaccgcgag cctgatgttc   1500
ttgttgagga gttcaacctg tttgataaca ataagtatgg tcacatcatt ggtgaggttg   1560
cttctaccca ccccaacggt ggaactggct ggagtggtaa ccttatgcct taccctggt   1620 ggatctctgg tgttggcgag gccgtcgctc tctgcggtta tgagcgcaac gccgatcgta   1680
ttcccggaac attctacgct cctatcctca agaacgagaa ccgttggcag tgggctatca   1740
ccatgatcca attcgccgcc gactccgcca tgaccacccg ctccaccagc tggtatgtct   1800
ggtcactctt cgcaggccac cccatgaccc atactctccc caccaccgcc gacttcgacc   1860
ccctctacta cgtcgctggt aagaacgagg acaagggaac tcttatctgg aagggtgctg   1920
cgtataacac caccaagggt gctgacgttc ccgtgtctct gtccttcaag ggtgtcaagc   1980
ccggtgctca agctgagctt actcttctga ccaacaagga gaaggatcct tttgcgttca   2040
atgatcctca caagggcaac aatgttgttg atactaagaa gactgttctc aaggccgatg   2100
gaaagggtgc tttcaacttc aagcttccta acctgagcgt cgctgttctt gagaccctca   2160
agaagggaaa gccttactct agctag                                        2186
```

PRODUCTION OF HIGH SOLIDS SYRUP FROM LIGNOCELLULOSIC BIOMASS HYDROLYSATE FERMENTATION BROTH

This Application claims the benefit of U.S. Provisional Application 61/328,799, filed Apr. 28, 2010 the entire content of which is incorporated herein by reference.

FIELD OF THE INVENTION

The invention relates to the field of fermentation process technology. Specifically, it has been discovered that a syrup having a viscosity of less than 100 centerpiece and containing at least about 40% solids can be produced in processing of lignocellulosic biomass hydrolysate fermentation broth.

BACKGROUND OF THE INVENTION

Cellulosic and lignocellulosic feedstocks and wastes, such as agricultural residues, wood, forestry wastes, sludge from paper manufacture, and municipal and industrial solid wastes, provide a potentially large renewable feedstock for the production of valuable products such as alcohols to be used as fuels, and other chemicals. Cellulosic and lignocellulosic feedstocks and wastes composed of carbohydrate polymers comprising cellulose, hemicellulose, and lignin are generally treated by a variety of chemical, mechanical and enzymatic means to release primarily hexose and pentose sugars in a hydrolysate which can be fermented to produce useful products using a biocatalyst.

In addition to the metabolizable sugars that are present in hydrolyzed biomass, the hydrolysate includes undigested lignin and other biomass components that carry through to product isolation and downstream processes. These hydrolysate components, mixed with the biocatalyst and other fermentation broth components, need to be processed in addition to the main product. Particularly in the production of fuel alcohols, where production volumes are very high, net water use is important as is the use of fossil energy to produce the fuel alcohol. To minimize net water use, fermentation broth with product removed may be recycled to earlier stages in the process, or solids may be separated from this broth and the liquid stream recycled to earlier stages in the process (referred to as back-set). Also, the liquid stream may be purified by various methods prior to recycle. The solid stream, containing a large percentage of lignin, has low nutritional value as an animal feed, but may be used as a fuel which is burned to provide energy in the overall production process.

For separation of liquid and solid fractions in the whole stillage of the corn grain dry milling process for ethanol production, which uses grain and not lignocellulosic biomass as a source of fermentable sugars, centrifugation is typically used. The high speed horizontal decanter type centrifuges typically used are not efficient in removing suspended solids. WO2008076716 discloses use of anionic polymer flocculants to improve agglomeration of solids in centrate from the centrifuges, to aid in subsequent solid/liquid separation. Using this process a thin stillage with little to no suspended solids may be achieved. US20080153149 discloses centrifugation followed by treatment of the resulting liquid fraction (thin stillage) in a fungal bioreactor. This process uses the thin stillage as a substrate for production of high value fungal biomass, and reusable process water is also obtained.

There remains a need for efficient, low-cost processes for treatment of production side streams from fermentation broth that includes lignocellulosic biomass hydrolysate, particularly where large volumes of liquid must be processed, to produce a recyclable liquid stream and usable solids streams.

SUMMARY OF THE INVENTION

The invention provides a processed syrup side product from a lignocellulosic biomass hydrolysate fermentation broth and a process for producing the syrup.

Accordingly, the invention provides a syrup comprising at least about 40% solids by weight and having a viscosity that is less than about 100 centipoise; wherein the syrup is the product of evaporation of the liquid fraction from a liquid/solid separation of lignocellulosic biomass hydrolysate fermentation broth.

In another embodiment the invention provides a process for producing a syrup comprising:
  a) providing a lignocellulosic biomass hydrolysate fermentation broth;
  b) optionally removing a product stream from the lignocellulosic biomass hydrolysate fermentation broth of (a) to produce a depleted broth;
  c) separating liquid and solid fractions from the broth of (a) or depleted broth of (b) to produce a thin stillage comprising less than about 0.1% suspended solids by weight; and
  d) evaporating the thin stillage of (c) to produce a syrup having at least about 40% solids by weight and viscosity that is less than about 100 centipoise.

In an alternate embodiment the invention provides a process for the production of ethanol comprising:
  a) providing a lignocellulosic biomass hydrolysate fermentation broth comprising an ethanol product;
  b) removing the ethanol from the lignocellulosic biomass hydrolysate fermentation broth of (a) by distillation to produce whole stillage;
  c) separating liquid and solid fractions from the whole stillage of (b) to produce a thin stillage comprising less than about 0.1% suspended solids by weight; and
  d) evaporating the thin stillage of (c) to produce a syrup comprising at least about 40% solids by weight and having a viscosity that is less than about 100 centipoise.

In another embodiment the invention provides a process for the production of butanol comprising:
  a) providing a lignocellulosic biomass hydrolysate fermentation broth comprising butanol product;
  b) extracting the butanol from the lignocellulosic biomass hydrolysate fermentation broth of (a) to produce a depleted broth;
  c) separating liquid and solid fractions from the depleted broth of (b) to produce a thin stillage with less than about 0.1% suspended solids by weight; and
  d) evaporating the thin stillage of (c) to produce a syrup comprising at least about 40% solids by weight and having a viscosity that is less than about 100 centipoise.

BRIEF DESCRIPTION OF THE SEQUENCES

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

SEQ ID numbers of coding regions and proteins of glycosyl hydrolases used in saccharification

| enzyme | SEQ ID NO: Amino acid | SEQ ID NO: coding |
|---|---|---|
| Xyn3 from *Trichoderma reesei* | 1 | 5 |
| Fv3 from *Fusarium verticillioides* | 2 | 6 |
| Fv43D from *Fusarium verticillioides* | 3 | 7 |
| Fv51A from *Fusarium verticillioides* | 4 | 8 |

INFORMATION ON DEPOSITED STRAINS

Applicants have made the following biological deposits under the terms of the Budapest Treaty on the International Recognition of the Deposit of Microorganisms for the Purposes of Patent Procedure:

| Depositor Identification Reference | International Depository Designation | Date of Deposit |
|---|---|---|
| *Zymomonas* ZW658 | ATCC No PTA-7858 | Sep. 12, 2006 |

DETAILED DESCRIPTION OF THE INVENTION

When lignocellulosic biomass hydrolysate is included in fermentation medium, the fermentation broth that results from production of a product by a biocatalyst in the medium is a complex slurry including a mixture of product, cells, lignin, and other biomass components. Processing side streams to useful materials is particularly important in production of products that are produced in relatively low amounts in fermentation broth, such as butanol and ethanol. Through steps disclosed herein, liquid and solid streams are efficiently processed, including production of a syrup that is at least about 40% solids. The syrup is high enough in solids to provide energy, when burned, which can be applied to the production process. The energy from the syrup, as well as purified water to be recycled, provide the overall production process with efficiency whereby commercial viability may be achieved.

The following definitions and abbreviations are to be use for the interpretation of the claims and the specification.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "fermentable sugar" refers to oligosaccharides and monosaccharides that can be used as a carbon source by a microorganism in a fermentation process.

The term "lignocellulosic" refers to a composition comprising both lignin and cellulose. Lignocellulosic material may also comprise hemicellulose.

The term "cellulosic" refers to a composition comprising cellulose and additional components, including hemicellulose.

The term "saccharification" refers to the production of fermentable sugars from polysaccharides.

The term "pretreated biomass" means biomass that has been subjected to pretreatment prior to saccharification. The pretreatment may take the form of physical, thermal or chemical means and combinations thereof.

The term "butanol" refers to isobutanol, 1-butanol, 2-butanol, or combinations thereof.

The term "lignocellulosic biomass" refers to any lignocellulosic material and includes materials comprising cellulose, hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Lignocellulosic biomass includes, but is not limited to, bioenergy crops, agricultural residues, municipal solid waste, industrial solid waste, sludge from paper manufacture, yard waste, wood and forestry waste. Examples of biomass include, but are not limited to, corn cobs, crop residues such as corn husks, corn stover, grasses, wheat straw, barley straw, hay, rice straw, switchgrass, waste paper, sugar cane bagasse, sorghum plant material, soybean plant material, components obtained from milling of grains, trees, branches, roots, leaves, wood chips, sawdust, shrubs and bushes, vegetables, fruits, and flowers.

The term "lignocellulosic biomass hydrolysate" refers to the product resulting from saccharification of lignocellulosic biomass. The biomass may also be pretreated or pre-processed prior to saccharification.

The term "lignocellulosic biomass hydrolysate fermentation broth" is broth containing product resulting from biocatalyst growth and production in a medium comprising lignocellulosic biomass hydrolysate. This broth includes components of lignocellulosic biomass hydrolysate that are not consumed by the biocatalyst, as well as the biocatalyst itself and product made by the biocatalyst.

The term "slurry" refers to a mixture of insoluble material and a liquid. A slurry may also contain a high level of dissolved solids. Examples of slurries include a saccharification broth, a fermentation broth, and a stillage.

The term "whole stillage" refers to the bottoms of a distillation. The whole stillage contains the high boilers and any solids of a distillation feed stream. Whole stillage is a type of depleted broth.

The term "thin stillage" refers to a liquid fraction resulting from solid/liquid separation of a whole stillage, fermentation broth, or product depleted fermentation broth.

The term "product depleted broth" or "depleted broth" refers herein to a lignocellulosic biomass hydrolysate fermentation broth after removal of a product stream.

The term "syrup" means a concentrated product produced from the removal of water, generally by evaporation, from thin stillage.

The term "filter cake resistance" or "specific cake resistance" refers to a heights specific value that quantifies the filterability of a slurry. The value is independent from slurry concentration, viscosity, pressure, and filtration area. The value is calculated using the Ruth equation and can be used to scale filtration equipment.

Ruth equation: $dt/dV=(\mu\alpha_{av}C/\Delta p)V+\mu R_m/\Delta p$ where t is filtration time (s), V is filtrate volume per unit filter area ($m^3/m^2$), $\Delta p$ is applied pressure for filtration (Pa), $\mu$ is liquid viscosity (kg/ms), $\mu\alpha_{av}$ is average specific cake resistance (m/kg), $R_m$ is filter medium resistance ($m^{-1}$), and C is cake mass formed per unit volume of filtrate ($kg/m^3$). See Yim et al. (Korean M. Chem. Eng., 18(5), 741, (2001)).

"Xyn3" is a GH10 family xylanase from *Trichoderma reesei*. Xyn3 (SEQ ID NO:1; coding SEQ ID NO:5) was shown to have endoxylanase activity indirectly by its ability to increase xylose monomer production in the presence of xylobiosidase when the enzymes set acts on pretreated biomass or on isolated hemicellulose.

"Fv3A" is a GH3 family enzyme from *Fusarium verticillioides*. Fv3A (SEQ ID NO:2; coding SEQ ID NO:6) was shown to have beta-xylosidase activity by assay with p-nitrophenyl-beta-xylopyranoside, xylobiose, mixed, linear xylo-oligomers and branched arabinoxylan oligomers from hemicellulose as substrates.

"Fv43D" is a GH43 family enzyme from *Fusarium verticillioides*. Fv43D (SEQ ID NO:3; coding SEQ ID NO:7) was shown to have beta-xylosidase activity by assay with p-nitrophenyl-beta-xylopyranoside, xylobiose, or mixed, linear xylo-oligomers as substrates.

"Fv51A" is a GH51 family enzyme from *Fusarium verticillioides*. Fv51A (SEQ ID NO:4; coding SEQ ID NO:8) was shown to have L-alpha-arabinofuranosidase activity by assay with p-nitrophenyl-alpha-L-arabinofuranoside and by the release of arabinose from the set of oligomers released from hemicellulose by the action of endoxylanase.

The term "target product" refers to any product that is produced by a microbial production host cell in a fermentation. Target products may be the result of genetically engineered enzymatic pathways in host cells or may be produced by endogenous pathways. Typical target products include but are not limited to acids, alcohols, alkanes, alkenes, aromatics, aldehydes, ketones, biopolymers, proteins, peptides, amino acids, vitamins, antibiotics, and pharmaceuticals.

Low Viscosity High Solids Syrup

The present invention relates to processing of side streams from a lignocellulosic biomass hydrolysate fermentation broth, particularly for producing a high solids syrup. The side streams are processed typically after product removal from the lignocellulosic biomass hydrolysate fermentation broth. The broth with product removed is a depleted broth. A lignocellulosic biomass hydrolysate fermentation broth or depleted broth is separated into solid and liquid fractions where the liquid fraction is a thin stillage. This thin stillage is very low in suspended solids. Due to the low suspended solids concentration in the thin stillage, it maintains a low viscosity during subsequent evaporation. The viscosity stays below about 100 centipoise throughout evaporation, allowing evaporation to at least about 40% solids or greater in the resulting syrup. Evaporation produces a syrup that is at least about 40%, 45%, 50%, 55%, 60%, 65%, or 70% solids. A syrup with at least about 40% solids can be burned to provide energy, while syrups with about 35% or lower solids do not provide more energy than is used to burn them.

In a typical corn grain dry grind ethanol production process (a process where grain and not lignocellulosic biomass is used as a source of fermentable sugars) the thin stillage has a much higher suspended solids concentration, becomes viscous during evaporation, and can only be evaporated to a syrup of less than 40% solids. The total suspended solids in the thin stillage from the dry grind process are typically about 2%-3%. In the present process, the thin stillage from a lignocellulosic biomass hydrolysate broth or depleted broth has less than 1,000 ppm, or 0.1%, suspended solids.

Being able to evaporate the thin stillage to a 40% or greater solids syrup also allows recovery of more water in evaporators that can then be recycled in the overall production process. At least about 60% of the water from the lignocellulosic biomass hydrolysate fermentation process may be recycled using the present process. The water recycled may be at least about 60%, 65%, 70%, 75%, 80%, 85%, 90%, or 95% of the water in the lignocellulosic biomass hydrolysate fermentation process. Recycle of water is especially important in lignocellulosic biomass hydrolysate fermentation for ethanol or butanol production due to the relatively high volume of broth that must be processed per volume of product obtained, and the high production volume which does not allow once through water use. Higher percent solids in syrup eliminates an additional drying step resulting in lower capital and operational costs.

Lignocellulosic Biomass Hydrolysate Fermentation Broth
Biomass Hydrolysate

Lignocellulosic biomass may be treated by any method known by one skilled in the art to produce fermentable sugars in a hydrolysate. Typically the biomass is pretreated using physical, thermal and/or chemical treatments, and saccharified enzymatically. Physical and chemical treatments include, but are not limited to, grinding, milling, cutting, base treatment such as with ammonia or NaOH, and acid treatment. Particularly useful is a low ammonia pretreatment where biomass is contacted with an aqueous solution comprising ammonia to form a biomass-aqueous ammonia mixture where the ammonia concentration is sufficient to maintain alkaline pH of the biomass-aqueous ammonia mixture but is less than about 12 weight percent relative to dry weight of biomass, and where dry weight of biomass is at least about 15 weight percent solids relative to the weight of the biomass-aqueous ammonia mixture, as disclosed in co-pending and commonly owned US Patent Application Publication US20070031918A1, which is herein incorporated by reference. Biomass is also typically reduced in particle size prior to pretreatment.

Enzymatic saccharification typically makes use of an enzyme consortium for breaking down cellulose and hemicellulose to produce a hydrolysate containing sugars including glucose, xylose, and arabinose. Saccharification enzymes are reviewed in Lynd, L. R., et al. (Microbiol. Mol. Biol. Rev., 66:506-577, 2002).

At least one enzyme is used, and typically a saccharification enzyme consortium is used that includes one or more glycosidases. Glycosidases hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem., 223:1-5, 1994; Eur. J. Biochem., 232:1-6, 1995; Eur. J. Biochem., 237:1-5, 1996; Eur. J. Biochem., 250:1-6, 1997; and Eur. J. Biochem., 264:610-650 1999, respectively]) of the general group "hydrolases" (EC 3.). Glycosidases useful in the present method can be categorized by the biomass component that they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabino-xylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), and feruloyl esterases (EC 3.1.1.73) to help release polysaccharides from other components of the biomass. It is well known in the art that microorganisms that produce polysaccharide-hydrolyzing enzymes often exhibit an activity, such as cellulose degradation, that is catalyzed by several enzymes or a group of enzymes having different substrate specificities. Thus, a "cellulase" from a microorganism may comprise a group of enzymes, all of which may contribute to the cellulose-degrading activity. Commercial or non-commercial enzyme preparations, such as cellulase, may comprise numerous enzymes depending on the purification scheme utilized to obtain the enzyme.

Saccharification enzymes may be obtained commercially, such as Spezyme® CP cellulase, Multifect® xylanase, Accellerase® 1500, and Accellerase® DUET (Danisco U.S. Inc., Genencor International, Rochester, N.Y.). In addition, saccharification enzymes may be unpurified and provided as a type of cell extract or whole cell preparation. The enzymes may be produced using recombinant microorganisms that have been engineered to express multiple saccharifying enzymes.

Of particular value in the present invention are classes of Glycoside hydrolases, such as the families GH3, GH39, GH43, GH55, GH10, and GH11. GHs are a group of enzymes that hydrolyze the glycosidic bond between two or more carbohydrates, or between a carbohydrate and a noncarbohydrate moiety. Families of GHs have been classified based on sequence similarity and are available in the Carbohydrate-Active enzyme (CAZy) database (Cantarel et al. (2009) Nucleic Acids Res. 37 (Database issue):D233-238). These enzymes are able to act on a number of substrates and are effective in the saccharification process. Glycoside hydrolase family 3 ("GH3") enzymes have a number of known activities: β-glucosidase (EC:3.2.1.21); β-xylosidase (EC: 3.2.1.37); N-acetyl β-glucosaminidase (EC:3.2.1.52); glucan β-1,3-glucosidase (EC:3.2.1.58); cellodextrinase (EC: 3.2.1.74); exo-1,3-1,4-glucanase (EC:3.2.1); and β-galactosidase (EC 3.2.1.23). Glycoside hydrolase family 39 ("GH39") enzymes have α-L-iduronidase (EC:3.2.1.76) or β-xylosidase (EC:3.2.1.37) activity. Glycoside hydrolase family 43 ("GH43") enzymes have the following activities: L-α-arabinofuranosidase (EC 3.2.1.55); β-xylosidase (EC 3.2.1.37); endoarabinanase (EC 3.2.1.99); and galactan 1,3-β-galactosidase (EC 3.2.1.145). Glycoside hydrolase family 51 ("GH51") enzymes have L-α-arabinofuranosidase (EC 3.2.1.55) or endoglucanase (EC 3.2.1.4) activity. Glycoside hydrolase family 10 ("GH10") are more fully described in Schmidt et al., 1999, Biochemistry 38:2403-2412 and Lo Leggio et al., 2001, FEBS Lett 509: 303-308) and the Glycoside hydrolase family 11 ("GH11") are more fully described in Hakouvainen et al., 1996, Biochemistry 35:9617-24.

Particularly useful in an enzyme consortium are the glycosyl hydrolases (GH) Xyn3, Fv3A, Fv51A and Fv43D. Xyn3 (SEQ ID NO:1) is a GH10 family xylanase from *Trichoderma reesei*, Fv3A (SEQ ID NO:2) is a GH3 family enzyme from *Fusarium verticillioides*, Fv43D (SEQ ID NO:3) is a GH43 family enzyme from *Fusarium verticillioides*, and Fv51A (SEQ ID NO:4) is a GH51 family of enzyme from *Fusarium verticillioides*.

These enzymes may be isolated from their natural host organism, or expressed in an engineered host organism for production. For example, a chimeric gene containing a promoter active in a target expression host cell, a sequence encoding a GH given above, and a termination signal is expressed from a plasmid vector or is integrated in the genome of a target expression host cell using standard methods known to one skilled in the art. A coding sequence used may be codon optimized for the specific host used for expression. Expression host cells typically used include bacteria such as *Escherichia, Bacillus, Lactobacillus, Pseudomonas* and *Streptomyces*, yeasts such as *Saccharomyces, Schizosaccharomyces, Candida, Hansenula, Pichia, Kluyveromyces,* and *Phaffia*, and filamentous fungi such as *Acremonium, Aspergillus, Aureobasidium, Bjerkandera, Ceriporiopsis, Chrysosporium, Coprinus, Coriolus, Corynascus, Chaertomium, Cryptococcus, Filobasidium, Fusarium, Gibberella, Humicola, Magnaporthe, Mucor, Myceliophthora, Mucor, Neocallimastix, Neurospora, Paecilomyces, Penicillium, Phanerochaete, Phlebia, Piromyces, Pleurotus, Scytaldium, Schizophyllum, Sporotrichum, Talaromyces, Thermoascus, Thielavia, Tolypocladium, Trametes,* and *Trichoderma*.

One skilled in the art would know how to determine the effective amount of enzymes to use in a consortium and adjust conditions for optimal enzyme activity. One skilled in the art would also know how to optimize the classes of enzyme activities required within a consortium to obtain optimal saccharification of a given pretreatment product under the selected conditions. An example of saccharification is described in US20070031918A1.

Prior to fermentation the saccharification mixture may be concentrated by evaporation, for example, to increase the concentration of fermentable sugars.

Optionally, liquid in the saccharification product may be separated from solids in a batch or continuous method. Optionally, the liquid or the entire saccharification product may be sterilized prior to fermentation. Depending on the biocatalyst(s) used during fermentation and the pH used during saccharification, the pH may be adjusted to that suitable for fermentation.

Lignocellulosic biomass hydrolysate containing fermentable sugars is included in fermentation medium typically as a percent of the medium, providing all or a portion of the carbon source for biocatalyst growth and product production. The hydrolysate in a lignocellulosic biomass hydrolysate fermentation medium is at least about 25% of the total volume, and may be at least about 25%, 30%, 35%, 40%, 45%, 50%, 55%, 60%, 65%, 70%, 75%, 80%, 85%, 90%, 95%, or greater. Examples of hydrolysate used as 40% or 80% of fermentation medium are given in Example 9 of US20070031918A1, which is herein incorporated by reference. Depending on the fermentable sugars concentration in the hydrolysate, additional sugars may be added to the medium. For example, when a hydrolysate containing about 80 g/L glucose and about 50 g/L xylose is included at 40% of the fermentation medium, additional glucose and xylose may be added to the desired final sugars concentrations. In addition to hydrolysate, fermentation medium may contain other nutrients, salts and factors required for growth and production by the specific biocatalyst to be used for product production, as well known to one skilled in the art. Supplements may include, for example, yeast extract, specific amino acids, phosphate, nitrogen sources, salts, and trace elements. Components required for production of a specific product made by a specific biocatalyst may also be included, such as an antibiotic to maintain a plasmid or a cofactor required in an enzyme catalyzed reaction. In fermentation media used herein, hydrolysate is 90% of the total volume.

In an alternative to preparing hydrolysate, adding it to fermentation medium, then carrying out the fermentation, a simultaneous saccharification and fermentation (SSF) process may be used to produce a lignocellulosic biomass hydrolysate fermentation broth. In this process sugars are produced from biomass as they are metabolized by the production biocatalyst.

Biocatalyst Fermentation and Target Products

Fermentable sugars in the lignocellulosic biomass hydrolysate fermentation medium are metabolized by suitable biocatalysts to produce target products. The sugars are contacted with a biocatalyst in a fermentation process where the biocatalyst is grown under conditions where a target product made by the biocatalyst is produced. Temperature and/or headspace gas may be adjusted for fermentation, depending on conditions useful for the particular biocatalyst(s) in use. Fermentation may be aerobic or anaerobic. These and other conditions including temperature and pH are adjusted for the particular biocatalyst used.

Typically the biocatalyst is engineered to produce a target product, but it may naturally produce a target product. Target products that may be produced by fermentation using a biocatalyst include, for example, acids, alcohols, alkanes, alkenes, aromatics, aldehydes, ketones, biopolymers, proteins, peptides, amino acids, vitamins, antibiotics, and pharmaceuticals. Alcohols include, but are not limited to, methanol, ethanol, propanol, isopropanol, butanol, ethylene glycol, propanediol, butanediol, glycerol, erythritol, xylitol, sorbitol, and 1,3-propanediol. Acids include, but are not limited to, acetic acid, lactic acid, propionic acid, 3-hydroxypropionic, butyric acid, gluconic acid, itaconic acid, citric acid, succinic acid and levulinic acid. Amino acids include glutamic acid, aspartic acid, methionine, lysine, glycine, arginine, threonine, phenylalanine and tyrosine. Additional target products include methane, ethylene, acetone and industrial enzymes. Particularly suitable products are ethanol and butanol, including isobutanol, 2-butanol, and 1-butanol.

The fermentation of sugars to target products may be carried out by one or more appropriate biocatalysts in single or multistep fermentations. Biocatalysts may be microorganisms selected from bacteria, filamentous fungi and yeast. Biocatalysts may be wild type microorganisms or recombinant microorganisms, and include, for example, *Escherichia, Zymomonas, Saccharomyces, Candida, Pichia, Streptomyces, Bacillus, Lactobacillus,* and *Clostridium.* In another embodiment, biocatalysts may be selected from the group consisting of recombinant *Escherichia coli, Zymomonas mobilis, Bacillus stearothermophilus, Saccharomyces cerevisiae, Clostridia thermocellum, Thermoanaerobacterium saccharolyticum,* and *Pichia stipitis*

Many biocatalysts used in fermentation to produce target products have been described and others may be discovered, produced through mutation, or engineered through recombinant means. Any biocatalyst that uses fermentable sugars in a lignocellulosic biomass hydrolysate medium may be used to make a target product(s) that it is known to produce, and thereby produce a lignocellulosic biomass hydrolysate broth for processing using the present process. Particularly useful for production in lignocellulosic biomass hydrolysate fermentation medium are alcohol products that may be used as fuels such as butanol and ethanol.

Fermentation of carbohydrates to acetone, butanol, and ethanol (ABE fermentation) by solventogenic *Clostridia* is well known (Jones and Woods (1986) Microbiol. Rev. 50:484-524). A fermentation process for producing high levels of butanol, also producing acetone and ethanol, using a mutant strain of *Clostridium acetobutylicum* is described in U.S. Pat. No. 5,192,673. The use of a mutant strain of *Clostridium beijerinckii* to produce high levels of butanol, also producing acetone and ethanol, is described in U.S. Pat. No. 6,358,717. Production of butanol by genetically modified yeast is disclosed for example in US 20070092957 A1. Genetically modified strains of *E. coli* have also been used as biocatalysts for ethanol production (Underwood et al., (2002) Appl. Environ. Microbiol.68:6263-6272). Ethanol has been produced by genetically modified *Zymomonas* in lignocellulosic biomass hydrolysate fermentation media (US 20070031918 A1). Genetically modified strains of *Zymomonas mobilis* with improved production of ethanol are described in US 2003/0162271 A1 and US 2009/0246846 A1.

Disclosed in U.S. Pat. No. 7,504,250 are recombinant microorganisms that produce 1,3-propanediol.

Lactic acid has been produced in fermentations by recombinant strains of *E. coli* (Zhou et al., (2003) Appl. Environ. Microbiol. 69:399-407), natural strains of *Bacillus* (US20050250192), and *Rhizopus oryzae* (Tay and Yang (2002) Biotechnol. Bioeng. 80:1-12). Recombinant strains of *E. coli* have been used as biocatalysts in fermentation to produce 1,3 propanediol (U.S. Pat. Nos. 6,013,494, 6,514, 733), and adipic acid (Niu et al., (2002) Biotechnol. Prog. 18:201-211). Acetic acid has been made by fermentation using recombinant *Clostridia* (Cheryan et al., (1997) Adv. Appl. Microbiol. 43:1-33), and newly identified yeast strains (Freer (2002) World J. Microbiol. Biotechnol. 18:271-275). Production of succinic acid by recombinant *E. coli* and other bacteria is disclosed in U.S. Pat. No. 6,159,738, and by mutant recombinant *E. coli* in Lin et al., (2005) Metab. Eng. 7:116-127). Pyruvic acid has been produced by mutant *Torulopsis glabrata* yeast (Li et al., (2001) Appl. Microbiol. Technol. 55:680-685) and by mutant *E. coli* (Yokota et al., (1994) Biosci. Biotech. Biochem. 58:2164-2167). Recombinant strains of *E. coli* have been used as biocatalysts for production of para-hydroxycinnamic acid (US20030170834) and quinic acid (US20060003429).

A mutant of *Propionibacterium acidipropionici* has been used in fermentation to produce propionic acid (Suwannakham and Yang (2005) Biotechnol. Bioeng. 91:325-337), and butyric acid has been made by *Clostridium tyrobutyricum* (Wu and Yang (2003) Biotechnol. Bioeng. 82:93-102). Propionate and propanol have been made by fermentation from threonine by *Clostridium* sp. strain 17cr1 (Janssen (2004) Arch. Microbiol. 182:482-486). A yeast-like *Aureobasidium pullulans* has been used to make gluconic acid (Anantassiadis et al., (2005) Biotechnol. Bioeng. 91:494-501), by a mutant of *Aspergillis niger* (Singh et al., (2001) Indian J. Exp. Biol. 39:1136-43). 5-keto-D-gluconic acid was made by a mutant of *Gluconobacter oxydans* (Elfari et al., (2005) Appl Microbiol. Biotech. 66:668-674), itaconic acid was produced by mutants of *Aspergillus terreus* (Reddy and Singh (2002) Bioresour. Technol. 85:69-71), citric acid was produced by a mutant *Aspergillus niger* strain (Ikram-UI-Haq et al., (2005) Bioresour. Technol. 96:645-648), and xylitol was produced by *Candida guilliermondii* FTI 20037 (Mussatto and Roberto (2003) J. Appl. Microbiol. 95:331-337). 4-hydroxyvalerate-containing biopolyesters, also containing significant amounts of 3-hydroxybutyric acid 3-hydroxyvaleric acid, were produced by recombinant *Pseudomonas putida* and *Ralstonia eutropha* (Gorenflo et al., (2001) Biomacromolecules 2:45-57). L-2,3-butanediol was made by recombinant *E. coli* (Ui et al., (2004) Lett. Appl. Microbiol. 39:533-537).

Production of amino acids by fermentation has been accomplished using auxotrophic strains and amino acid analog-resistant strains of *Corynebacterium, Brevibacterium*, and *Serratia*. For example, production of histidine using a strain resistant to a histidine analog is described in Japanese Patent Publication No. 56008596 and using a recombinant strain is described in EP 136359. Production of tryptophan using a strain resistant to a tryptophan analog is described in Japanese Patent Publication Nos. 47004505 and 51019037. Production of isoleucine using a strain resistant to an isoleucine analog is described in Japanese Patent Publication Nos. 47038995, 51006237, 54032070. Production of phenylalanine using a strain resistant to a phenylalanine analog is described in Japanese Patent Publication No. 56010035. Production of tyrosine using a strain requiring phenylalanine for growth, resistant to tyrosine (Agr. Chem. Soc. Japan 50 (1) R79-R87 (1976), or a recombinant strain (EP263515, EP332234), and production of arginine using a strain resistant to an L-arginine analog (Agr. Biol. Chem. (1972) 36:1675-1684, Japanese Patent Publication Nos. 54037235 and 57150381) have been described. Phenylalanine was also produced by fermentation in *Eschericia coli* strains ATCC 31882, 31883, and 31884. Production of glutamic acid in a recombinant coryneform bacterium is described in U.S. Pat. No. 6,962,805. Production of threonine by a mutant strain of *E. coli* is described in Okamoto and Ikeda (2000) J. Biosci Bioeng. 89:87-79. Methionine was produced by a mutant strain of *Corynebacterium Ilium* (Kumar et al, (2005) Bioresour. Technol. 96: 287-294).

Useful peptides, enzymes, and other proteins have also been made by biocatalysts (for example, in U.S. Pat. Nos. 6,861,237, 6,777,207, 6,228,630).

To grow well and have high product production in a lignocellulosic biomass hydrolysate fermentation broth, a biocatalyst may be selected or engineered to have higher tolerance to inhibitors present in biomass hydrolysate such as acetate. For example, improving utilization of xylose and production of ethanol under stress conditions such as those encountered in a lignocellulosic biomass hydrolysate fermentation broth by *Zymomonas* is disclosed in commonly owned and co-pending US Patent Application Publication US20110014670, which is herein incorporated by reference. Disclosed therein is continuous growth of *Zymomonas* cells in medium containing xylose, acetate, ammonium acetate, and ethanol and isolation of improved *Zymomonas* strains such as ZW705.

Preparation of High Solids Syrup from Liqnocellulosic Biomass Hydrolysate Fermentation Broth Side streams are processed from a lignocellulosic biomass hydrolysate fermentation broth after removing a product stream containing the product produced by a biocatalyst. For example when butanol is the product, it may be removed from the fermentation broth by extracting the fermentation broth such as by gas stripping, or using a water immiscible organic extractant and separating the butanol-containing organic phase from the aqueous phase as disclosed in commonly owned and co-pending WO 2009/149270, which is herein incorporated by reference. The resulting broth with product removed is a depleted broth. When ethanol is the product, the broth is distilled, typically using a beer column, to generate an ethanol product stream and a whole stillage, which is a depleted broth. Distillation may be using any conditions known to one skilled in the art including at atmospheric or reduced pressure. Alternatively, the product may be removed from the solid or liquid fraction after separation.

The broth or depleted broth, such as whole stillage, is separated into solid and liquid streams, where the liquid stream called thin stillage has less than about 0.1% suspended solids. Any separation process that produces a thin stillage having less than about 0.1% suspended solids may be used. Various filtration devices may be used such as a belt filter, belt press, screw press, drum filter, disc filter, Nutsche filter, filter press or filtering centrifuge. Filtration may be aided such as by application of vacuum, pressure, or centrifugal force. In addition, a combination of separation processes may be used to achieve low suspended solids concentration, such as centrifugation followed by a small filter press to remove suspended solids that remain after centrifugation.

A portion of initially separated liquid may be re-separated. For example when filtering, some initial filtrate may be recycled back to the filter feed tank at the beginning of filtration to improve the thin stillage quality. The initial 5%-10% of filtrate may have suspended solids of about 0.1%. However the remaining 90%-95% of filtrate typically has much lower suspended solids and thus the average for the thin stillage will be substantially less than 0.1% of suspended solids even without initial filtrate recycle.

To improve efficiency of filtration, a heat treatment may be used as disclosed in commonly owned and co-pending U.S. Patent Application #61/328,804, which is herein incorporated by reference. The lignocellulosic biomass hydrolysate fermentation broth or depleted broth, such as whole stillage, may be treated with heat under conditions where the filter cake resistance of the broth or depleted broth, such as whole stillage, is reduced by at least about 20%. The broth or depleted broth, such as whole stillage, is treated at a temperature that is between about 70° C. and about 150° C. for a time that is between about 30 seconds and 210 minutes. Longer times are used with lower temperatures in the range, and shorter times are used with higher temperatures in the range. For example, in Example 2 and 4 of U.S. Patent Application #61/328,804, heating at 70° C. for 60 minutes was sufficient to reduce filter cake resistance by 24%; heating at 110° C. for 30 seconds was sufficient to reduce filter cake resistance by 21%; and a 30 second 145° C. treatment reduced filter cake resistance by 45%. Particularly useful are temperatures between about 95° C. and about 150° C. where shorter times are effective such as between about 30 seconds and 30 minutes. Whole stillage from an atmospheric distillation, which is typically carried out at between 95° C. to 100° C., may be maintained at that temperature for about fifteen to 30 minutes. As in this case, if the temperature of the whole stillage, or other depleted broth, or broth is at or above the desired temperature due to a previous process step, no further application of heat may be required; the temperature is maintained for the desired time by holding the whole stillage or other depleted broth, or broth in an insulated vessel for the required period of time. For a short treatment, particularly useful are temperatures between about 110° C. and about 150° C. for times between about 30 seconds and two minutes. Treating with heat may be carried out in any system capable of maintaining temperature for the desired time. For example, heating may be in a heat jacketed vessel or in a heat exchanger with subsequent hold in a vessel or pipe loop.

The time required to reduce filter cake resistance by at least about 20%, at a given temperature, may also vary depending on the pH of the broth, depleted broth or whole stillage for treatment as disclosed in U.S. Patent Application #61/328, 804. Greater reduction in filter cake resistance is achieved at lower pH, with pH of 6 or lower being particularly useful. Depending on the biocatalyst used in fermentation, the pH of the lignocellulosic biomass hydrolysate fermentation broth may already be at pH 6 or lower. Alternatively, the pH of the broth, depleted broth or whole stillage may be adjusted to about 6, 5, 4, or 3 prior to or during heat treatment. It may be useful to mix or stir the depleted broth or whole stillage during pH adjustment for even distribution of pH adjusting acid. In addition, mixing may be used during heat treatment for even temperature control. Mixing, which may be continuous or non-continuous, is typically performed by an agitator system such as one using impellers.

Following liquid/solid separation of a heat treated lignocellulosic biomass hydrolysate fermentation broth or depleted broth, the solids fraction, or wetcake, may be burned to supply energy to the production process. The wetcake may be dried prior to burning, such as by air drying, to reduce moisture.

A product stream may be removed following liquid/solid filtration of a heat treated lignocellulosic biomass hydrolysate fermentation broth. For example, the liquid stream may be extracted or distilled to generate a product stream, such as distillation to produce an ethanol product stream and a remaining liquid.

Following liquid/solid separation, a portion of the liquid fraction may be recycled for use directly as back set. As back set, the liquid could be added at any point in the process where fresh water is needed, such as in pretreatment, saccharification, or biocatalyst seed production. The remainder, or all, of the liquid fraction is further purified by evaporation producing water that can be recycled and a syrup. Due to the low suspended solids concentration in the liquid fraction, or thin stillage, it maintains a low viscosity in a subsequent evaporation step. The viscosity stays below about 100 centipoise throughout evaporation, allowing evaporation to produce a syrup with at least about 40% total solids, which is a combination of suspended and dissolved solids. The viscosity is related to the % total solids, pH and temperature as demonstrated in Example 3 herein. For example, a viscosity below 100 centipoise is maintained with evaporation to about 67% solids, with pH of 5.7 and at 60° C.; while at a pH of 4.7 a 69.5% solids syrup maintains viscosity below 100 centipoise at 40° C. Evaporation may be at pressure, at atmospheric pressure, or with reduced pressure.

The resulting syrup with at least about 40% solids can be burned to provide energy, with no additional drying step required. Syrups that are typically produced in corn grain dry grind ethanol processes have about 35% or lower solids and do not provide more energy than is used in drying, then burning them.

Evaporation may be in any evaporation system, such as falling film, rising film, forced circulation, plate or mechanical and thermal vapor recompression systems. Evaporation may be continuous or batch and may use a multi-effect evaporator. The evaporated water may be recycled in the overall lignocellulosic biomass hydrolysate fermentation process.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "s" is second, "min" means minute(s), "h" of "hr" means hour(s), "µL" means microliter(s), "mL" means milliliter(s), "L" means liter(s), "m" is meter, "nm" means nanometer(s), "mm" means millimeter(s), "cm" means centimeter(s), "µm" means micrometer(s), "mM" means millimolar, "M" means molar, "mmol" means millimole(s), "µmole" means micromole(s), "g" means gram(s), "µg" means microgram(s), "mg" means milligram(s), "kg" is kilogram, "rpm" means revolutions per minute, "C" is Centigrade, "ppm" means parts per million, "cP" is centipoise.

General Methods:
Saccharification Enzymes

Accellerase® 1500 (A1500) and Multifect® Xylanase were obtained from Danisco U.S. Inc., Genencor, International (Rochester, N.Y.).

Cellulase and Hemicellulase Production Strain

Strain 229: A *Trichoderma reesei* strain, derived from RL-P37 (Sheir-Neiss and Montenecourt, 1984, Appl. Microbiol. Biotechnol. 20:46-53) through mutagenesis and selection for high cellulase production, was co-transformed with the β-glucosidase expression cassette (cbh1 promoter, *T. reesei* β-glucosidase) gene, cbh1 terminator, and amdS marker), and the endoxylanase expression cassette (cbh1 promoter, *T. reesei* xyn3, and cbh1 terminator) using PEG mediated transformation (Penttila et al., 1987, Gene 61(2):155-64). Numerous transformants were isolated and examined for β-glucosidase and endoxylanase production. One transformant, referred to as *T. reesei* strain #229, was used in certain studies described herein.

Strain H3A: *T. reesei* strain #229 was co-transformed with the β-xylosidase Fv3A expression cassette (cbh1 promoter, Fv3A gene, cbh1 terminator, and alsR marker), the β-xylosidase Fv43D expression cassette (egl1 promoter, Fv43D gene, native Fv43D terminator), and the Fv51A α-arabinofuranosidase expression cassette (egl1 promoter, Fv51A gene, Fv51A native terminator) using electroporation. Transformants were selected on Vogels agar plates containing chlorimuron ethyl. Numerous transformants were isolated and examined for β-xylosidase and L-α-arabinofuranosidase production. *T. reesei* integrated expression strain H3A, which recombinantly expresses *T. reesei* β-glucosidase 1, *T. reesei* xyn3, Fv3A, Fv51A, and Fv43D was isolated."

Extra cellular protein produced during fermentation of strain H3A was separated from the cell mass by centrifugation, concentrated by membrane-ultrafiltration through a Millipore 10 kD molecular cut off weight membrane and pH adjusted to 4.8. Total protein was determined using a modified Biuret method as modified by Weichselbaum and Gornall using Bovine Serum Albumin as a calibrator (Weichselbaum, 1960, Amer. J. Clin. Path. 16:40; Gornall et al., 1949 J. Biol. Chem. 177:752). This H3A extracellular protein preparation, called herein H3A protein, was used as a combination cellulase and hemicellulase preparation effecting complex carbohydrate hydrolysis during SSF.

Biocatalyst and Inoculum Preparation

Origin of the *Zymomonas mobilis* Strains Used in Fermentation

A lignocellulosic biomass hydrolysate fermentation broth that isprocessed as in these examples may be made using alternative biocatalysts. Exemplary strains are used in these examples and are described below. As an alternative, strain ZW658, deposited as ATCC #PTA-7858, may be used to produce a lignocellulosic biomass hydrolysate fermentation broth for processing.

*Zymomonas mobilis* strain ZW705 was produced from strain ZW801-4 by the methods detailed in US Patent Application Publication US2011-0014670, which is herein incorporated by reference, as briefly restated here. Cultures of *Z. mobilis* strain ZW801-4 were grown under conditions of stress as follows. ZW801-4 is a recombinant xylose-utilizing strain of *Z. mobilis* that was described in U.S. Pat. No. 7,741,119, which is herein incorporated by reference. Strain ZW801-4 was derived from strain ZW800, which was derived from strain ZW658, all as described in U.S. Pat. No. 7,741,119. ZW658 was constructed by integrating two operons, PgapxylAB and Pgaptaltkt, containing four xylose-utilizing genes encoding xylose isomerase, xylulokinase, transaldolase and transketolase, into the genome of ZW1 (ATCC #31821) via sequential transposition events, and followed by adaptation on selective media containing xylose. ZW658 was deposited as ATCC #PTA-7858. In ZW658, the gene encoding glucose-fructose oxidoreductase was insertionally-inactivated using host-mediated, double-crossover, homologous recombination and spectinomycin resistance as a selectable marker to create ZW800. The spectinomycin resistance marker, which was bounded by loxP sites, was removed by site specific recombination using Cre recombinase to create ZW801-4.

A continuous culture of ZW801-4 was run in 250 ml stirred, pH and temperature controlled fermentors (Sixfors; Bottmingen, Switzerland). The basal medium for fermentation was 5 g/L yeast extract, 15 mM ammonium phosphate, 1 g/L magnesium sulfate, 10 mM sorbitol, 50 g/L xylose and 50 g/L glucose. Adaptation to growth in the presence of high concentrations of acetate and ammonia was effected by gradually increasing the concentration of ammonium acetate added to the above continuous culture media while maintaining an established growth rate as measured by the specific dilution rate over a period of 97 days. Ammonium acetate was increased to a concentration of 160 mM. Further increases in ammonium ion concentration were achieved by addition of ammonium phosphate to a final total ammonium ion concentration of 210 mM by the end of 139 days of continuous culture. Strain ZW705 was isolated from the adapted population by plating to single colonies and amplification of one chosen colony.

Strain AR3 7-31 was produced from strain ZW705 by further adaptation for growth in corn cob hydrolysate medium as disclosed in commonly owned and co-pending U.S. Patent Application 61/424,077, which is incorporated herein by reference. ZW705 was grown in a turbidostat (U.S. Pat. No. 6,686,194; Heurisko USA, Inc. Newark, Del.), which is a continuous flow culture device where the concentration of cells in the culture was kept constant by controlling the flow of medium into the culture, such that the turbidity of the culture was kept within specified narrow limits. Two media were available to the growing culture in the continuous culture device, a resting medium (Medium A) and a challenge medium (Medium B). A culture was grown on resting medium in a growth chamber to a turbidity set point and then was diluted at a dilution rate set to maintain that cell density. Dilution was performed by adding media at a defined volume once every 10 minutes. When the turbidostat entered a media challenge mode, the choice of adding challenge medium or resting medium was made based on the rate of return to the set point after the previous media addition. The steady state concentration of medium in the growth chamber was a mix of Medium A and Medium B, with the proportions of the two media dependent upon the rate of draw from each medium that allowed maintenance of the set cell density at the set dilution rate. A sample of cells representative of the population in the growth chamber was recovered from the outflow of the turbidostat (in a trap chamber) at weekly intervals. The cell sample was grown once in MRM3G6 medium and saved as a glycerol stock at −80° C.

ZW705 was grown to an arbitrary turbidity set point that dictated that the culture use all of the glucose and approximately half of the xylose present in the incoming media to meet the set point cell density at the set dilution rate. Using resting medium that was 50% HYAc/YE and 50% MRM3G6.5X4.5NH$_4$Ac12.3 and challenge medium that was HYAc/YE. A strain isolated after 3 weeks was used in another round of turbidostat adaptation using HYAc/YE as the resting medium and HYAc/YE+9 weight % ethanol as the challenge medium. Strain AR3 7-31 was isolated after 2 weeks and was characterized as a strain with improved xylose and glucose utilization, as well as improved ethanol production, in hydrolysate medium. By sequence analysis, AR3 7-31 was found to have a mutation in the *Zymomonas mobilis* genome ORF encoding a protein having characteristics of a membrane transport protein, and annotated as encoding a fusaric acid resistance protein.

Media

MRM3 contains per liter: yeast extract (10 g), KH$_2$PO$_4$ (2 g) and MgSO$_4$.7H$_2$O (1 g)

MRM3G6 contains is MRM3 containing 60 g/L glucose

MRM3G6.5X4.5NH$_4$Ac12.3 is MRM3 containing 65 g/L glucose, 45 g/L xylose, 12.3 g/L ammonium acetate HYAc/YE contains cob hydrolysate from which solids were removed by centrifugation and that was filter sterilized containing 68 g/L glucose, 46 g/L xylose and 5 g/L acetate, supplemented with 6.2 g/L ammonium acetate and 0.5% yeast extract, adjusted to pH5.8.

Specific Cake Resistance

The specific cake resistance quantifies the resistance change of the filter cake per heights unit cake. It is independent from slurry concentration, viscosity, pressure and filtration area. The value results from the Ruth equation as described above [see Yim et al., Korean M. Chem. Eng., 18(5), 741, (2001)].

Details of Viscosity Measurements

Viscosity was measured by a Paar Physica MCR 300 Rheometer, which allows for full temperature control. The measurement principle applied to the corn biomass samples is a rotational measurement using a cone-cone or double-gap type of measurement head. Measurements are performed at different temperatures (20° C., 40° C., 60° C.) and in a ramp from 1-300 1/s shear rate. The viscosity reported is the infinite shear viscosity.

Evaporation

A lab-scale evaporation set up was used comprising a recirculating heating bath filled with Syltherm heat transfer fluid connected to a 5 L jacketed round bottom flask. A short path distillation head with double condensers was used for overheads cooling. About 1 to 2 kg of thin stillage was used in evaporation. Overhead water and bottoms syrup samples were collected at regular time intervals.

Filtration—460 mm Netzsch FilterPress

The following commercially available pre-pilot scale press was used:

Netzsch 470/SP membrane filter press Mix Pack Membrane with 1.0 Pre Squeeze capacity (ANDRITZ AG, Stattegger Strasse 18, A-8045 Graz, Austria). Manual Piping with proper number of valves for feed, core blow, cake blow, membrane blow back and filtrate block are included.

The 470 mm press is used in a liquid/solids separation. The equipment consists of two operating skids; the first has two agitated feed tanks and air pumps to feed the press, the second cart is the press itself.

Filter area: 6800 cm$^2$
number of chambers: 2
max. filtration pressure=7 bar (700 kilopascal)
max. operating temperature 85° C.
closing mechanism: hydraulic ram
feed supply: air driven diaphragm pump
dimensions: 1300×1500×600 mm
weight: approx. 250 kg The press handles fluids under pressure. The slurry is fed to the press at up to 100 psi (689.5 kilopascal). There is a hydraulic ram that compresses the filter plate stack at 6,000 psi (41.4 megapascal). There is also a separate air cylinder that provides up to 225 psi (1551.3 kilopascal) squeezing pressure to the press for mechanical compression.

Example 1

Production of Lignocellulosic Biomass Hydrolysate Fermentation Broth

Pretreatment for Corn Cob
Fermentation Batch FRF 6

A Jaygo horizontal paddle reactor (approximately 170 L) was used to pretreat 4 batches of cob pieces, all sizes <½" (1.27 cm). Cobs were charged to the reactor and vacuum was applied to the vessel to reach 0.1 bar (10 kilopascal) absolute prior to introduction of ammonium hydroxide solution to give about 4 (2 batches), 6 (1 batch) or 8 (1 batch) wt % NH$_3$ relative to dry weight biomass. Steam was added to give a temperature of about 145° C. This temperature was held for 20 minutes. At the end of pretreatment, the reactor was depressurized in a controlled fashion to reach atmospheric pressure, and then vacuum was subsequently applied to bring the pressure in the vessel back to about 0.1 bar (10 kilopascal) absolute. Pretreated cobs pieces exiting the reactor were about 55 wt % dry biomass. Cob pieces were reduced to less than 1 mm in a micropulverizer (Model #1 SH, Serial #10019; Pulverizing Machinery Division of Mikropul Corporation; Summit, N.J.) with a 1.0 mm screen.

Fermentation Batches FRF 7-10

A horizontal Littleford Day 130 L reactor vessel containing a jacket for passing steam around the body of the vessel and one of the sides (Littleford Day, Inc., Florence, Ky.) was used for pretreatment of batches of cob. For each batch, the vessel was loaded with cob (less than 1 mm in size). The cob had been reduced in size by treating in a micropulverizer (Model #1SH, Serial #10019; Pulverizing Machinery Division of Mikropul Corporation; Summit, N.J.) with a 1.0 mm screen. The % moisture of the cob used in different pretreatment batches is given in Table 2.

Vacuum was applied to the vessel to reach 0.1 atm prior to introduction of a 28.9 wt % ammonium hydroxide solution and water near the top of the vessel to give a 6 wt % NH$_3$ relative to dry weight biomass. Steam was introduced near the top of the vessel to raise the internal vessel temperature to 145° C. This temperature was held for 20 minutes. At the end of pretreatment, the reactor was depressurized through a vent condenser to reach atmospheric pressure. Vacuum (approximately to less than 1 atm) was subsequently applied for 15 minutes to lower the temperature to less than 60° C. The final % solids for each pretreatment batch are given in Table 2, along with the fermentation batch that each pretreatment batch was used in.

TABLE 2

Cob, pretreatment and fermentation batches.

| Cob % moisture | Pretreat batch | Wt % solids final | Fermentation batch |
|---|---|---|---|
| 5.9 | SSL 9 | 53.1 | 7 |
| 5.9 | SSL 10 | 65.7 | 7 |
| 5.9 | SSL 11 | 71.3 | 7 |
| 5.9 | SSL 12 | 71.9 | 7 |
| 5.9 | SSL 13 | 69.8 | 8 |
| 5.9 | SSL 14 | 67.6 | 8 |
| 5.9 | SSL 15 | 68.9 | 8 |
| 5.2 | SSL 18 | 65.1 | 9 |
| 5.2 | SSL 19 | 68.1 | 9 |
| 5.2 | SSL 20 | 68.1 | 9 |
| 8.0 | SSL 24 | 61.1 | 10 |
| 8.0 | SSL 25 | 66.7 | 10 |
| 8.0 | SSL 26 | 67.8 | 10 |

Saccharification Runs for FRF 6-10

Saccharification was carried out in a 200 L Sartorius Biostat D200 for 72 hr except #9 was for 24 hr. Solids loading was 20% to 25%. pH of pretreated cob biomass was adjusted to 5.3 with H$_2$SO$_4$. Enzymes added were a consortium of A1500, Xyn3, Fv3A, Fv51A, and Fv43D that was added at 21.3 mg protein/g glucan+xylan for #6-9, except in Run #6 Multifect® Xylanase was substituted for of Xyn3, and in Run #10 H3A extract (described in General Methods) was used at 14 mg/g glucan+xylan. Saccharification was run at 47° C.

Seed Culture Preparation 2 mL of frozen strain ZW705 stock (strain described in General Methods) was grown in MRM3G6 (10 g/L BBL yeast extract, 2 g/L KH$_2$PO$_4$, 1 g/L MgSO$_4$.7H$_2$O, 60 g/L glucose) at 33° C., without shaking for 8 hr as a revival culture. Shake flasks containing 1 L of MRM3G10 media (same as MRM3G6 but with 100 g/L glucose) were inoculated with 20 mL of revival culture, and incubated at 33° C. with shaking for 13-16 hr. Growth was to an OD$_{600}$ between 1.5 and 3.1. Sufficient shake flask culture was used to inoculate 10 L seed fermenters to an initial OD$_{600}$ of 0.1 (FRF 7-10) or 0.35 (FRF6).

Seed fermentations in MaxSMG20 or MaxSGM15 (20 g/L yeast extract, 2 g/L KH$_2$PO$_4$, 5 g/L MgSO$_4$*7H$_2$O, 10 mM sorbitol, and 200 g/L glucose. Seed fermentations were performed at 33° C. and pH 5.8 (FRF6 & 7) or 5.5 (FRF 8-10). Seed was harvested after first observation of glucose reduction to less than 85 g/L, with glucose measured by using a YSI 2700 SELECT™ Biochemistry Analyzer (YSI Life Sciences; Yellow Springs, Ohio).

Fermentation

Fermentation batches listed in Table 2 were run in a 200 L Sartorius Biostat D200 containing 180 L of biomass hydrolysate and 20 L of ZW705 seed culture. pH was adjusted to 5.8 with NaOH. Runs were maintained at 30° C.-33° C. for 80 hr (FRF 6, 7), 90 hr (FRF 8, 10) or 120 hr (FRF 9).

Example 2

Composition of Thin Stillaqe from Liqnocellulosic Corn Cob Biomass

Hydrolysate Fermentation Broth

Fermentation broth batches were generated using pretreatment, saccharification, and fermentation as described in Example 1. Different fermentation batch feeds were distilled under different conditions as given in Table 3 using a continuous distillation column. Samples of the fermentation broth for batch 10 (10-1, 10-2) were adjusted to the lower pHs given in Table 3 by addition of 98% sulfuric acid. Distillation residence time in the column was about 8 minutes.

An ethanol stream was collected from the distillation column. The whole stilllage from the distillation column was filtered at 60° C. using a filter press as described in General Methods. A heat treatment was applied to some of the batches as given in Table 3.

The thin stillage samples from the filtration were analyzed for total solids (including dissolved and suspended solids) and suspended solids. Total solids were determined by heating the sample in a vacuum or convection oven at 80° C. for 24-72 hrs until dry. The weight of each dried sample was expressed as a percent of the original weight of the sample. Suspended solids were determined by following ASTM D5907-09. The thin stillage samples were shown to have 5-7% total solids and about 100-750 ppm suspended solids for various batches as given in Table 3.

TABLE 3

Preparation details and results for different fermentation broth feed batches.

| Batch | Distillation | Heat Treatment | % Total solids in thin stillage | Suspended solids in thin stillage (ppm) |
|---|---|---|---|---|
| 7 | 760 mm Hg; Feed/Steam = 4.5; pH = 6.1 | No heat treatment | 5.6 | 242 |
| 8 | 760 mm Hg; Feed/Steam = 5.3; Feed pH = 6.3 | Overnight holdup at 40° C.; Heat Treatment 3hrs at 95° C. | 6.3 | 200 |
| 9 | 760 mm Hg; Feed/Steam = 4.5; Feed pH = 5.4 | Heat Treatment 95° C. for 3 hrs | 5 | 200 |
| 10-1 | 760 mm Hg; Feed/Steam = 4.5; Feed pH = 6.1 | Heat Treatment 95° C. for 1 hr | 6.8 | 713 |
| 10-2 | 760 mm Hg; Feed/Steam = 4.5; Feed pH = 5.1 | Heat Treatment 95° C. for 1 hr | 7 | 746 |

Example 3

Effect of pH and Temperature of Thin Stillage on Viscosity of Syrup Following Evaporation to Different Percent Solids A lab scale evaporation set-up as described in General Methods was used to evaporate water from thin stillage. Thin stillage samples from fermentation broth batches 7-10, prepared as described in Examples 1 and 2, were evaporated under different pressure conditions as given in Table 4. Samples of thin stillage were pH adjusted by addition of either 50% NaOH or 98% sulfuric acid to give the sample pH values in Table 4. Overhead water and bottom syrup samples were collected at different % total solids. Initial % total solids for thin stillage samples was between 5% and 7% as in Example 2. Viscosities of the syrup samples were measured at different temperatures (20° C., 40° C., and 60° C.) in a ramp from 1-300 1/s shear rate. Infinite shear viscosity numbers are reported in Table 4. The syrup samples measured were Newtonian at temperatures and concentrations shown in Table 4. Percent total solids were determined for each sample by drying in a vacuum oven or convection oven at 80° C. for 24 to 48 hrs.

Viscosity for all samples, including samples with about 70% solids, remained below 100 centipoise at 60° C. With reduced pH, samples with up to about 70% solids had viscosities below 100 centipoise at 40° C.

TABLE 4

Viscosities of syrup samples from thin stillage evaporated to different % solids content

| Batch | Evaporation Conditions | % Total solids | Viscosity (cP) 20° C. | 40° C. | 60° C. | 80° C. |
|---|---|---|---|---|---|---|
| 7 | 1 atm (101.325 kilopascal); Feed pH = 5.7 | 7.5% | 2.19 | 1.21 | 1.36 | nd* |
|   |   | 14.0% | 2.99 | 1.60 | 1.65 | nd |
|   |   | 24.4% | 5.59 | 3.31 | 2.42 | nd |
|   |   | 36.8% | 14.31 | 8.43 | 4.59 | nd |
|   |   | 67.4% | 330.00 | 124.00 | 72.80 | nd |
| 7 | 0.2 atm (20.265 kilopascal); Feed pH = 5.6 | 5.8% | 1.43 | 0.95 | 0.79 | nd |
|   |   | 12.3% | 2.02 | 1.34 | 0.91 | nd |
|   |   | 20.4% | 3.56 | 2.04 | 1.51 | nd |
|   |   | 29.8% | 7.97 | 4.60 | 2.87 | nd |
|   |   | 36.9% | 18.10 | 9.10 | 5.02 | nd |
| 8 | 0.2 atm (20.265 kilopascal); Feed pH = 5.6 | 6.7% | 1.42 | 1.09 | 0.93 | nd |
|   |   | 15.0% | 2.62 | 1.78 | 1.25 | nd |
|   |   | 33.1% | 13.65 | 7.17 | 4.88 | nd |
|   |   | 61.8% | 925.89 | 257.46 | 84.68 | nd |
| 8 | 1 atm (101.325 kilopascal); Feed pH = 5.4 | 8.7% | 2.42 | 1.46 | 1.41 | nd |
|   |   | 17.5% | 3.85 | 1.86 | 1.66 | nd |
|   |   | 64.5% | 650.00 | 239.47 | 94.38 | nd |
| 8 | 1 atm (101.325 kilopascal); Feed pH = 4.7 | 6.4% | 1.65 | 0.99 | 0.91 | nd |
|   |   | 11.8% | 2.02 | 1.04 | 0.96 | nd |
|   |   | 32.7% | 5.23 | 3.20 | 2.04 | nd |
|   |   | 42.3% | 13.14 | 5.82 | 4.35 | nd |
|   |   | 69.5% | 230.59 | 84.20 | 42.34 | nd |
| 8 | 0.2 atm (20.265 kilopascal); Feed pH = 4.7 | 6.2% | 1.49 | 1.19 | 0.88 | nd |
|   |   | 10.5% | 1.75 | 1.23 | 0.82 | nd |
|   |   | 21.2% | 3.65 | 2.50 | 1.36 | nd |
|   |   | 34.5% | 13.79 | 7.05 | 4.86 | nd |
|   |   | 48.3% | 81.12 | 35.32 | 19.54 | nd |
| 8 | 0.2 atm (20.265 kilopascal); Feed pH = 6.5 | 7.0% | 1.65 | 0.99 | 0.88 | nd |
|   |   | 10.0% | 1.88 | 1.14 | 0.88 | nd |
|   |   | 18.9% | 3.22 | 1.74 | 1.55 | nd |
|   |   | 31.0% | 8.34 | 4.73 | 2.74 | nd |
|   |   | 56.9% | 108.84 | 38.76 | 18.89 | nd |
| 8 | 2.3 atm (233.0475 kilopascal); Feed pH = 5.4 | 6.1% | 1.49 | 1.13 | 0.71 | nd |
|   |   | 8.4% | 1.57 | 1.17 | 0.73 | nd |
|   |   | 14.0% | 2.20 | 1.29 | 1.10 | nd |
|   |   | 45.0% | 25.17 | 12.15 | 6.74 | nd |
| 9 | 1 atm (101.325 kilopascal); Feed pH = 4.8 | 4.9% | 1.43 | 0.93 | 0.81 | 0.55 |
|   |   | 8.0% | 1.61 | 1.16 | 0.68 | 0.65 |
|   |   | 27.0% | 5.23 | 3.23 | 1.79 | 1.77 |
|   |   | 42.8% | 19.65 | 10.13 | 5.80 | 4.49 |
|   |   | 71.3% | 298.88 | 82.64 | 32.79 | 13.86 |
| 10-1 | 0.2 atm (20.265 kilopascal); Feed pH = 5.7 | 7.9% | 1.72 | 1.09 | 0.90 | 0.62 |
|   |   | 11.6% | 2.05 | 1.64 | 0.89 | 0.69 |
|   |   | 30.2% | 8.92 | 4.48 | 2.89 | 2.41 |
|   |   | 47.1% | 106.35 | 39.53 | 18.49 | 13.95 |

TABLE 4-continued

Viscosities of syrup samples from thin stillage evaporated to different % solids content

| Batch | Evaporation Conditions | % Total solids | Viscosity (cP) | | | |
|---|---|---|---|---|---|---|
| | | | 20° C. | 40° C. | 60° C. | 80° C. |
| 10-2 | 0.2 atm (20.265 kilopascal); Feed pH = 5.0 | 6.9% 11.8% 30.2% 41.0% | 1.69 2.26 10.90 29.23 | 0.93 1.19 6.03 14.47 | 0.92 1.05 3.58 8.66 | 0.57 0.79 3.02 6.51 |
| 10-1 | 2.3 atm (233.0475 kilopascal); Feed pH = 5.7 | 9.0% 14.6% 42.9% | 1.81 2.08 20.45 | 0.94 1.62 11.79 | 0.91 0.86 5.20 | 0.53 1.14 5.02 |
| 10-2 | 2.3 atm (233.0475 kilopascal); Feed pH = 5.1 | 9.8% 16.2% 43.8% | 1.87 2.01 20.09 | 1.09 1.37 11.17 | 0.99 0.83 6.54 | 0.61 0.87 4.90 | nd* = not determined

Example 4

Viscosities of Syrup from Corn Stover Hydrolysate Fermentation Broth Following Evaporation of Thin Stillage to Different Percent Solids For sample DF1062, 2nd pass corn stover was milled to ⅜" (0.95 cm). Pretreatment was done at 140° C. with 14% NH₃ and 65% solids for 60 min. Saccharification was done at 47° C., pH 5.3, with 7.8 mg/g glucan+xylan of an enzyme consortium, for 96 hr. Saccharification enzymes were a mix of cellulases and hemicellulases expressed in a *Trichoderma reesei* strain derived from RL-P37 (Sheir-Neiss and Montenecourt (1984) Appl. Microbiol. Biotechnol. 20:46-53), similar to the strain H3A preparation described in General Methods, which could also be used. For sample DF1065, 2nd pass chp-stalk stover was milled to ⁵⁄₆₄" (0.2 cm). Pretreatment was done at 140° C. with 8% NH₃ and 55% solids for 20 min. Saccharification was done at 47° C., pH 5.3, 7.8 mg/g glucan+xylan of the same enzyme consortium, for 96 hr.

For fermentation, 10 mM sorbitol was added to the hydrolysates, and the pH was adjusted to 5.8, before fermentation. DF1062 and DF1065 were fermented with 10 vol % (final volume) harvest-ready ZW705 seed, at pH 5.8, at 33° C., shifted to 30° C. after 23.5 hr. The seed was grown in halfYEMaxSMG15 medium (10 g/L yeast extract, 2 g/L KH₂PO₄, 5 g/L MgSO₄.7H₂O, 10 mM sorbitol, 150 g/L glucose) at 33° C., pH 5.5, to allow ~125 g/L glucose consumption. Different fermentation batches were distilled in a lab distillation unit at 1 atmosphere for 3 hrs. The whole stilllage from the distillation column was filtered using a lab scale filtration unit. A lab scale evaporation set-up was used to evaporate water from thin stillage at 1 atmosphere. Overhead water and bottom syrup samples were collected at different % total solids. Viscosities of the syrup samples were measured at different temperatures (20° C., 40° C., and 60° C.) in a ramp from 1-300 1/s shear rate. Viscosities reported are at 100 1/s shear rate in Table 5. Percent suspended solids were determined as in Example 2. Total percent solids were determined using a meter instrument. The sample was heated to 105° C. in 30 sec. Percent total solids was reported when a mean weight loss of 1 mg was not exceeded after 240 seconds at 105° C. Measured total suspended solids for thin stillage samples were low (at limit of detection). Both thin stillage samples had a pH of 5.7.

TABLE 5

Viscosities of syrup samples from thin stillage evaporated to different % solids content

| Batch | Evaporation Conditions | % Total solids | Viscosity (cP) | | | |
|---|---|---|---|---|---|---|
| | | | 20° C. | 40° C. | 60° C. | 80° C. |
| DF1062 | 1 atm (101.325 kilopascal); Feed pH = 5.7 | 11.2% 21.9% 53.9% | 2.02 4.91 61.20 | 1.42 3.05 26.84 | 1.23 2.18 14.49 | 0.87 1.53 9.19 |
| DF1065 | 1 atm (101.325 kilopascal); Feed pH = 5.65 | 8.8% 21.2% 41.7% | 2.22 5.25 28.06 | 1.54 3.21 14.33 | 1.25 2.29 9.01 | 0.85 1.52 6.33 |

Example 5

Viscosities of Syrup from Switchgrass Hydrolysate Fermentation Broth Following Evaporation of Thin Stillage to Different Percent Solids For sample DF1102 and DF1119 samples switchgrass was milled to <1 mm. Pretreatment was done at 155° C. with 12% NH₃ for 60 min. Saccharification was done at 47° C., pH 5.3, with 14 mg/g glucan+xylan of an enzyme consortium, for 94 hr. Saccharification enzymes were a mix of cellulases and hemicellulases expressed in a *Trichoderma reesei* strain derived from RL-P37 (Sheir-Neiss and Montenecourt (1984) Appl. Microbiol. Biotechnol. 20:46-53), similar to the strain H3A preparation described in General Methods, which could also be used. For fermentation, 10 mM sorbitol was added to the hydrolysates, and the pH was adjusted to 5.8, before fermentation. DF1102 was fermented with 10 vol % (final volume) harvest-ready AR3 7-31 strain seed, at pH 5.8, at 33° C., shifted to 30° C. after 21 hr.

The seed was grown in halfYEMaxSMG15 media (10 g/L yeast extract, 2 g/L KH2PO4, 5 g/L MgSO4*7H2O, 10 mM sorbitol, 150 g/L glucose) at 33 C, pH 5.5, to allow ~125 g/L glucose consumption. Different fermentation batches were distilled in a lab distillation unit at 1 atmosphere for 3 hrs. The whole stilllage from the distillation column was filtered using a lab scale filtration unit. A lab scale evaporation set-up was used to evaporate water from thin stillage at 1 atmosphere. Overhead water and bottom syrup samples were collected at different % total solids. Viscosities of the syrup samples were measured at different temperatures (20° C., 40° C., and 60° C.) in a ramp from 1-300 1/s shear rate. Viscosities reported are at 100 1/s shear rate in Table 6. Measured total suspended solids for thin stillage was 0.26%. Percent suspended and total solids were determined as in Example 4. Thin stillage samples had pH of 5.7.

TABLE 6

Viscosities of syrup samples from thin stillage evaporated to different % solids content

| Batch | Evaporation Conditions | % Total solids | Viscosity (cP) | | | |
|---|---|---|---|---|---|---|
| | | | 20° C. | 40° C. | 60° C. | 80° C. |
| DF1102 | 1 atm (101.325 kilopascal); Feed pH = 5.6 | 6.3% 22.6% 33.1% | 1.80 4.91 10.95 | 1.21 2.95 6.26 | 0.98 2.00 4.06 | 0.96 1.69 3.31 |
| DF1119 | 1 atm (101.325 kilopascal); Feed pH = 5.5 | 53.4% | 99.32 | 38.76 | 22.89 | 18.42 |

What is claimed is:

1. A syrup comprising at least about 40% solids by weight and having a viscosity that is less than about 100 centipoise, and derived from stillage comprising less than about 0.1% suspended solids; wherein the syrup is the product of evaporation of the liquid fraction from a liquid/solid separation of lignocellulosic biomass hydrolysate fermentation broth or product depleted lignocellulosic biomass hydrolysate fermentation broth.

2. The syrup of claim 1 wherein the lignocellulosic biomass hydrolysate fermentation broth comprises a target product selected from the group consisting of acids, alcohols, alkanes, alkenes, aromatics, aldehydes, ketones, biopolymers, proteins, peptides, amino acids, vitamins, antibiotics, and pharmaceuticals.

3. The syrup of claim 2 wherein the target compound is selected from the group consisting of ethanol, butanol and 1,3-propanediol.

4. The syrup of claim 1 wherein the lignocellulosic biomass hydrolysate fermentation broth is produced from biomass that is selected from the group consisting of switchgrass, waste paper, sludge from paper manufacture, corn cobs, corn husks, corn stover, grasses, wheat, wheat straw, hay, barley straw, rice straw, sugar cane bagasse, components obtained from processing of grains, trees, branches, roots, leaves, wood chips, sawdust, shrubs and bushes, vegetables, fruits, and flowers.

5. The syrup of claim 1 wherein the percent solids is at least about 45%.

6. The syrup of claim 1 wherein the percent solids is at least about 50%.

7. A process for the production of a target product comprising:
   a) providing a lignocellulosic biomass hydrolysate fermentation broth comprising a target product;
   b) removing the target product from the lignocellulosic biomass hydrolysate fermentation broth of (a) by distillation to produce whole stillage;
   c) separating liquid and solid fractions from the whole stillage of (b) to produce a thin stillage comprising less than about 0.1% suspended solids by weight; and
   d) evaporating the thin stillage of (c) to produce a syrup comprising at least about 40% solids by weight and having a viscosity that is less than about 100 centipoise.

8. The process of claim 7 wherein the target product is selected from the group consisting of ethanol, butanol and 1,3-propanediol.

9. The process of claims 7 wherein the syrup is burned without further drying.

10. The process of claim 7 wherein water from evaporating the thin stillage is recycled.

11. The process of claim 7 wherein the lignocellulosic biomass hydrolysate fermentation broth of (a) or the depleted broth or whole stillage of (b) has a pH of about 6 or lower.

12. The process of claim 7 wherein the lignocellulosic biomass hydrolysate fermentation broth of (a) or the depleted broth or whole stillage of (b) is treated with heat for between about 30 seconds and about 210 minutes at a temperature that is between about 70° C. and about 150° C., with time and temperature inversely related.

13. The process of claim 7 wherein the lignocellulosic biomass hydrolysate fermentation broth is produced from biomass selected from the group consisting of switchgrass, waste paper, sludge from paper manufacture, corn cobs, corn husks, corn stover, grasses, wheat, wheat straw, hay, barley straw, rice straw, sugar cane bagasse, components obtained from processing of grains, trees, branches, roots, leaves, wood chips, sawdust, shrubs and bushes, vegetables, fruits, and flowers.

14. The process of claim 7 wherein the percent solids of the syrup is at least about 45%.

15. The process of claim 7 wherein the percent solids of the syrup is at least about 50%.

* * * * *